(12) United States Patent
Faltys et al.

(10) Patent No.: US 11,730,964 B2
(45) Date of Patent: Aug. 22, 2023

(54) PULSE GENERATION AND STIMULATION ENGINE SYSTEMS

(71) Applicant: Presidio Medical, Inc., South San Francisco, CA (US)

(72) Inventors: Michael A. Faltys, San Francisco, CA (US); Aaron Hardinger, San Francisco, CA (US); James Harris, San Francisco, CA (US); Douglas Michael Ackermann, Reno, NV (US); Kenneth S. Wu, San Francisco, CA (US)

(73) Assignee: Presidio Medical, Inc., South San Francisco, CA (US)

(*) Notice: Subject to any disclaimer, the term of this patent is extended or adjusted under 35 U.S.C. 154(b) by 0 days.

(21) Appl. No.: 17/779,037

(22) PCT Filed: Nov. 24, 2020

(86) PCT No.: PCT/US2020/062077
§ 371 (c)(1),
(2) Date: May 23, 2022

(87) PCT Pub. No.: WO2021/102448
PCT Pub. Date: May 27, 2021

(65) Prior Publication Data
US 2022/0409905 A1 Dec. 29, 2022

Related U.S. Application Data

(60) Provisional application No. 62/965,772, filed on Jan. 24, 2020, provisional application No. 62/939,666, filed on Nov. 24, 2019.

(51) Int. Cl.
*A61N 1/36* (2006.01)
*A61N 1/20* (2006.01)

(52) U.S. Cl.
CPC .......... *A61N 1/36171* (2013.01); *A61N 1/20* (2013.01)

(58) Field of Classification Search
CPC .............................. A61N 1/36171; A61N 1/20
See application file for complete search history.

(56) References Cited

U.S. PATENT DOCUMENTS

| 4,057,069 A | 11/1977 | Dorffer et al. |
| 4,917,093 A | 4/1990 | Dufresne et al. |
| 5,034,589 A | 7/1991 | Evans et al. |

(Continued)

FOREIGN PATENT DOCUMENTS

| DE | 4324185 | 1/1995 |
| EP | 0 281 717 | 9/1988 |

(Continued)

OTHER PUBLICATIONS

International Search Report and Written Opinion in PCT Application No. PCT/US2020/062077 dated Feb. 17, 2021 in 18 pages.

(Continued)

*Primary Examiner* — Joseph M Dietrich
(74) *Attorney, Agent, or Firm* — Knobbe, Martens, Olson & Bear, LLP

(57) ABSTRACT

Disclosed herein are systems and methods that can involve a neuromodulation device configured to perform in multiple electrical modulation modes with a single architecture.

21 Claims, 12 Drawing Sheets

(56) References Cited

U.S. PATENT DOCUMENTS

| | | |
|---|---|---|
| 5,833,714 A | 11/1998 | Loeb |
| 5,868,743 A | 2/1999 | Saul et al. |
| 6,139,545 A | 10/2000 | Utley et al. |
| 6,189,536 B1 | 2/2001 | Martinez et al. |
| 6,192,279 B1 | 2/2001 | Barreras et al. |
| 6,205,359 B1 | 3/2001 | Bovega |
| 6,293,266 B1 | 9/2001 | Getting |
| 6,366,813 B1 | 4/2002 | DiLorenzo |
| 6,600,956 B2 | 7/2003 | Maschino et al. |
| 6,671,561 B1 | 12/2003 | Moaddeb |
| 6,819,956 B2 | 11/2004 | DiLorenzo |
| 6,895,280 B2 | 5/2005 | Meadows et al. |
| 6,907,295 B2 | 6/2005 | Gross et al. |
| 6,937,893 B2 | 8/2005 | Danz et al. |
| 6,974,533 B2 | 12/2005 | Zhou |
| 6,975,907 B2 | 12/2005 | Zanakis et al. |
| 7,079,903 B2 | 7/2006 | O'Brien |
| 7,216,001 B2 | 5/2007 | Hacket et al. |
| 7,421,299 B2 | 9/2008 | Frericks et al. |
| 7,428,438 B2 | 9/2008 | Parramon et al. |
| 7,437,193 B2 | 10/2008 | Parramon et al. |
| 7,502,652 B2 | 3/2009 | Gaunt et al. |
| 7,519,428 B1 * | 4/2009 | Palmer ............... A61N 1/36125 607/57 |
| 7,587,241 B2 | 9/2009 | Parramon et al. |
| 7,638,032 B2 | 12/2009 | Zhou et al. |
| 7,691,252 B2 | 4/2010 | Zhou et al. |
| 7,742,828 B2 | 6/2010 | Gadsby et al. |
| 7,780,833 B2 | 8/2010 | Hawkins et al. |
| 7,881,808 B2 | 2/2011 | Borgaonkar et al. |
| 7,891,085 B1 | 2/2011 | Kuzma et al. |
| 7,909,764 B1 | 3/2011 | Wenzel et al. |
| 8,019,439 B2 | 9/2011 | Kuzma et al. |
| 8,034,229 B2 | 10/2011 | Zhou et al. |
| 8,121,703 B1 | 2/2012 | Palmer |
| 8,135,478 B2 | 3/2012 | Gross |
| 8,271,098 B2 | 9/2012 | Swanson et al. |
| 8,359,102 B2 | 1/2013 | Alataris et al. |
| 8,406,886 B2 | 3/2013 | Gaunt et al. |
| 8,417,352 B2 | 4/2013 | Carroll et al. |
| 8,509,903 B2 | 8/2013 | York et al. |
| 8,644,933 B2 | 2/2014 | Ozawa et al. |
| 8,646,172 B2 | 2/2014 | Kuzma et al. |
| 8,650,747 B2 | 2/2014 | Kuzma et al. |
| 8,712,533 B2 | 4/2014 | Alataris et al. |
| 8,768,472 B2 | 7/2014 | Fang et al. |
| 8,792,988 B2 | 7/2014 | Alataris et al. |
| 8,897,895 B2 | 11/2014 | Mashiach |
| 8,948,881 B2 | 2/2015 | Fisk |
| 8,983,614 B2 | 3/2015 | Kilgore et al. |
| 9,008,780 B2 | 4/2015 | Nudo et al. |
| 9,008,781 B2 | 4/2015 | Ahmed |
| 9,008,800 B2 | 4/2015 | Ackermann et al. |
| 9,011,310 B2 | 4/2015 | Ahmed |
| 9,037,248 B2 | 5/2015 | Durand et al. |
| 9,072,886 B2 | 7/2015 | Gaunt et al. |
| 9,119,966 B2 | 9/2015 | Franke et al. |
| 9,205,265 B2 | 12/2015 | Franke |
| 9,283,391 B2 | 3/2016 | Ahmed |
| 9,327,125 B2 | 5/2016 | Alataris et al. |
| 9,333,356 B2 | 5/2016 | Franke et al. |
| 9,333,357 B2 | 5/2016 | Alataris et al. |
| 9,364,661 B2 | 6/2016 | Kilgore et al. |
| 9,370,664 B2 | 6/2016 | Marnfeldt et al. |
| 9,381,350 B2 | 7/2016 | Ahmed |
| 9,384,990 B2 | 7/2016 | Musa |
| 9,387,322 B2 | 7/2016 | Bhadra et al. |
| 9,393,423 B2 | 7/2016 | Parramon et al. |
| 9,403,014 B2 | 8/2016 | Kilgore et al. |
| 9,480,842 B2 | 11/2016 | Alataris et al. |
| 9,492,665 B2 | 11/2016 | Khalil et al. |
| 9,498,621 B2 | 11/2016 | Ackermann et al. |
| 9,572,979 B2 | 2/2017 | Fridman et al. |
| 9,694,181 B2 | 7/2017 | Bhadra et al. |
| 9,707,390 B2 | 7/2017 | Ahmed |
| 9,707,391 B2 | 7/2017 | Ahmed |
| 9,782,593 B2 | 10/2017 | Parramon et al. |
| 9,789,329 B2 | 10/2017 | Ahmed |
| 9,821,157 B2 | 11/2017 | Ahmed et al. |
| 9,844,668 B2 | 12/2017 | Ahmed |
| 9,889,291 B2 | 2/2018 | Bhadra et al. |
| 10,071,241 B2 | 9/2018 | Bhadra et al. |
| 10,195,434 B2 | 2/2019 | Bhadra et al. |
| 10,272,240 B2 | 4/2019 | Ackermann et al. |
| 10,441,782 B2 | 10/2019 | Bhadra et al. |
| 11,027,126 B2 | 6/2021 | Ackermann et al. |
| 2002/0015963 A1 | 2/2002 | Keen |
| 2003/0040785 A1 | 2/2003 | Maschino et al. |
| 2004/0181261 A1 | 9/2004 | Manne |
| 2004/0215285 A1 | 10/2004 | Pollock |
| 2005/0075709 A1 | 4/2005 | Brennen et al. |
| 2006/0085048 A1 | 4/2006 | Cory et al. |
| 2006/0095088 A1 | 5/2006 | Ridder |
| 2006/0167527 A1 | 7/2006 | Femano et al. |
| 2006/0184211 A1 | 8/2006 | Gaunt et al. |
| 2006/0265027 A1 | 11/2006 | Vaingast et al. |
| 2007/0027490 A1 | 2/2007 | Ben-Haim et al. |
| 2007/0043400 A1 | 2/2007 | Donders et al. |
| 2007/0060815 A1 | 3/2007 | Martin et al. |
| 2007/0073354 A1 | 3/2007 | Knudson et al. |
| 2007/0083193 A1 | 4/2007 | Werneth et al. |
| 2007/0255319 A1 | 11/2007 | Greenberg et al. |
| 2007/0291522 A1 | 12/2007 | Toba et al. |
| 2008/0208287 A1 | 8/2008 | Palermo et al. |
| 2008/0208300 A1 | 8/2008 | Pasch et al. |
| 2009/0149797 A1 | 6/2009 | Dacey, Jr. et al. |
| 2009/0192567 A1 | 7/2009 | Armstrong et al. |
| 2009/0254148 A1 | 10/2009 | Borgens et al. |
| 2011/0021943 A1 | 1/2011 | Lacour et al. |
| 2011/0071590 A1 | 3/2011 | Mounaim et al. |
| 2011/0077660 A1 | 3/2011 | Janik et al. |
| 2011/0160798 A1 | 6/2011 | Ackermann et al. |
| 2011/0190849 A1 | 8/2011 | Faltys et al. |
| 2011/0192720 A1 | 8/2011 | Blauw et al. |
| 2011/0221438 A1 | 9/2011 | Goodwill et al. |
| 2012/0016226 A1 | 1/2012 | Gertner |
| 2012/0053510 A1 | 3/2012 | Peters et al. |
| 2012/0277830 A1 | 11/2012 | Arfin et al. |
| 2013/0035745 A1 | 2/2013 | Ahmed et al. |
| 2013/0053922 A1 | 2/2013 | Ahmed et al. |
| 2013/0238048 A1 | 9/2013 | Almendiger et al. |
| 2013/0274842 A1 | 10/2013 | Guant et al. |
| 2014/0031905 A1 | 1/2014 | Irazoqui et al. |
| 2014/0119480 A1 | 5/2014 | Keegan |
| 2014/0128865 A1 | 5/2014 | Gross |
| 2014/0324129 A1 | 10/2014 | Franke et al. |
| 2015/0045675 A1 | 2/2015 | Chernomorsky |
| 2015/0073406 A1 | 3/2015 | Molsberger |
| 2015/0165210 A1 | 6/2015 | Kilgore et al. |
| 2015/0174397 A1 | 6/2015 | Bhadra et al. |
| 2015/0182742 A1 | 7/2015 | Ackermann et al. |
| 2015/0238764 A1 | 8/2015 | Franke |
| 2015/0293192 A1 | 10/2015 | Schmidt et al. |
| 2015/0316499 A1 | 11/2015 | Jacks et al. |
| 2016/0101286 A1 | 4/2016 | Bhadra et al. |
| 2016/0158542 A1 | 6/2016 | Ahmed |
| 2016/0235969 A1 | 8/2016 | Kilgore et al. |
| 2016/0235990 A1 | 8/2016 | Mashiach |
| 2016/0243353 A1 | 8/2016 | Ahmed |
| 2016/0256689 A1 | 9/2016 | Vallejo et al. |
| 2016/0263381 A1 | 9/2016 | Ahmed et al. |
| 2016/0271392 A1 | 9/2016 | Vallejo et al. |
| 2016/0271413 A1 | 9/2016 | Vallejo et al. |
| 2016/0331326 A1 | 11/2016 | Xiang et al. |
| 2016/0346533 A1 | 12/2016 | Bhadra et al. |
| 2017/0028192 A1 | 2/2017 | Ahmed et al. |
| 2017/0050024 A1 | 2/2017 | Bhadra et al. |
| 2017/0080244 A1 | 3/2017 | Chiel et al. |
| 2017/0100591 A1 | 4/2017 | Nudo et al. |
| 2017/0136235 A1 | 5/2017 | Molsberger |
| 2017/0312505 A1 | 11/2017 | Ahmed |
| 2018/0028824 A1 | 1/2018 | Pivonka et al. |
| 2018/0256886 A1 | 9/2018 | Bhadra et al. |
| 2018/0361155 A1 | 12/2018 | Bhadra et al. |

(56) References Cited

U.S. PATENT DOCUMENTS

| | | |
|---|---|---|
| 2019/0060640 A1 | 2/2019 | Bhadra et al. |
| 2019/0167996 A1 | 6/2019 | Bhadra et al. |
| 2019/0184160 A1 | 6/2019 | Franke et al. |
| 2019/0184173 A1 | 6/2019 | Franke |
| 2019/0269921 A1 | 9/2019 | Bhadra et al. |
| 2020/0001073 A1 | 1/2020 | Bhadra et al. |
| 2020/0129767 A1 | 4/2020 | Yoshida et al. |
| 2021/0038101 A1 | 2/2021 | Wu et al. |
| 2022/0088374 A1 | 3/2022 | Ackermann et al. |
| 2022/0096827 A1 | 3/2022 | Ackermann et al. |
| 2022/0176130 A1 | 6/2022 | Wu et al. |

FOREIGN PATENT DOCUMENTS

| | | |
|---|---|---|
| EP | 2 942 023 | 11/2015 |
| WO | WO 1998/15317 | 4/1998 |
| WO | WO 2007/082382 | 7/2007 |
| WO | WO 2008/048321 | 4/2008 |
| WO | WO 2008/140376 | 11/2008 |
| WO | WO 2010/042750 | 4/2010 |
| WO | WO 2013/188753 | 12/2013 |
| WO | WO 2015/142838 | 9/2015 |
| WO | WO 2017/044542 | 3/2017 |
| WO | WO 2017/062272 | 4/2017 |
| WO | WO 2017/106519 | 6/2017 |
| WO | WO 2018/085611 | 5/2018 |
| WO | WO 2018/187237 | 10/2018 |
| WO | WO 2019/157285 | 8/2019 |
| WO | WO 2019/164952 | 8/2019 |
| WO | WO 2020/010020 | 1/2020 |
| WO | WO 2021/102447 | 5/2021 |
| WO | WO 2021/102448 | 5/2021 |

OTHER PUBLICATIONS

Ackermann, Jr, D. Michael, et al. "Separated interface nerve electrode prevents direct current induced nerve damage." Journal of neuroscience methods 201.1 (2011): 173-176.

Bhadra, Niloy, and Kevin L. Kilgore. "Direct current electrical conduction block of peripheral nerve." IEEE Transactions on Neural Systems and Rehabilitation Engineering 12.3 (2004): 313-324.

Borsook, David. "A future without chronic pain: neuroscience and clinical research." Cerebrum: the Dana forum on brain science. vol. 2012. Dana Foundation, 2012.

Brummer, S.B. et al. "Electrical Stimulation of the Nervous System: The Principle of Safe Charge Injection with Noble Metal Electrodes." Bioelectrochemistry and Bioenergetics 2: (1975) 13-25.

Bussel, Catelijne M., Dirk L. Stronks, and Frank JPM Huygen. "Successful treatment of intractable complex regional pain syndrome type I of the knee with dorsal root ganglion stimulation: a case report." Neuromodulation: Technology at the Neural Interface 18.1 (2015): 58-61.

Cogan, S.F., et al. "In Vitro Comparison of the Charge-Injection Limits of Activated Iridium Oxide (AIROF) and Platinum-Iridium Microelectrodes", IEEE Transactions on Biomedical Engineering, 52.9 (2005): 1612-1614.

Cogan, S.F., et al. "Potential-Biased, Asymmetric Waveforms for Charge-Injection With Activated Iridium Oxide (AIROF) Neural Stimulation Electrodes." 2006: 53(2): 327-332.

Donaldson et al. "When are actively balanced biphasic ('Lilly') stimulating pulses necessary in a neurological prosthesis?" Medical & Biological Engineering & Computing Jan. 1986: 24: 41-49.

ElBasiouny, S., et al. Modulation of motoneuronal firing behavior after spinal cord injury using intraspinal microstimulation current pulses: a modeling study. J. Appl. Physiol. 103 (2007) 276-286.

Fridman, Gene Y., and Charles C. Della Santina. "Safe direct current stimulation to expand capabilities of neural prostheses." IEEE Transactions on Neural Systems and Rehabilitation Engineering 21.2 (2013): 319-328.

Fridman, Gene Y., and Charles C. Della Santina. "Safe direct current stimulator 2: concept and design." In Engineering in Medicine and Biology Society (EMBC), 2013 35th Annual International Conference of the IEEE, pp. 3126-3129. IEEE, 2013.

Gabrielsson, Erik O., et al. "A four diode full wave ionic current rectifier based on bipolar membranes: Overcoming the limit of electrode capacity." Advanced Materials 26.30 (2014): 5143-5147.

Hasegawa, G., et al. "Impact of Electrolyte on Pseudocapacitance and Stability of Porous Titanium Nitride (TiN) Monolithic Electrode", Journal of The Electrochemical Society, 162.1 (2015): A77-A85.

Hollingworth, Milo, et al. "Single Electrode Deep Brain Stimulation with Dual Targeting at Dual Frequency for the Treatment of Chronic Pain: A Case Series and Review of the Literature." Brain sciences 7.1 (2017): 1-11.

Holtzheimer, Paul E., and Helen S. Mayberg. "Deep brain stimulation for psychiatric disorders." Annual review of neuroscience 34 (2011): 289-307.

Huang, C. et al. "Electrical stimulation of the auditory nerve: direct current measurement in vivo." IEEE Transactions on Biomed. Eng. vol. 46 No. Apr. 4, 1999 at 461-470.

Hurlbert, R. John. "Dose-response study of the pathologic effects of chronically applied direct current stimulation on the normal rat spinal cord." J. Neurosurg. 79 (Dec. 1993) 905-916.

Keifer, Orion Paul, Jonathan P. Riley, and Nicholas M. Boulis. "Deep brain stimulation for chronic pain: intracranial targets, clinical outcomes, and trial design considerations." Neurosurgery Clinics 25.4 (2014): 671-692.

Krum, Henry, et al. "Catheter-based renal sympathetic denervation for resistant hypertension: a multicentre safety and proof-of-principle cohort study." The Lancet 373.9671 (2009): 1275-1281.

Kim et al. "Electrochemical studies on the alternating current corrosion of mild steel under cathodic protection condition in marine environments", Electrochimica Acta 51, 2006, p. 5259-5267.

Kumsa, D et al. Electrical neurostimulation with imbalanced waveform mitigates dissolution of platinum Electrodes. J. Neural Eng. 13 (2016): 1-5.

Kumsa, D et al. Electrical neurostimulation with imbalanced waveform mitigates dissolution of platinum electrodes. Neural Eng. (2018) 13(5): 1-8.

Kumsa, D.W., et al. "Electron transfer processes occurring on platinum neural stimulating electrodes: pulsing experiments for cathodic-first, charge-imbalanced, biphasic pulses for $0.566 < k < 2.3$ in rat subcutaneous tissues", Journal of Neural Engineering, 16 (2019): 1-11.

McHardy, J., et al., "An Approach to Corrosion Control during Electrical Stimulation", Annals of Biomedical Engineering, 5 (1977): 144-149.

Mendell, Lorne M. "Constructing and deconstructing the gate theory of pain." PAIN® 155.2 (2014): 210-216.

Merrill, Daniel R., Marom Bikson, and John GR Jefferys. "Electrical stimulation of excitable tissue: design of efficacious and safe protocols." Journal of neuroscience methods 141.2 (2005): 171-198.

Mortimer, J.T., et al., "Intramuscular Electrical Stimulation: Tissue Damage", Annals of Biomedical Engineering, 8 (1980): 235-244.

Nahin, Richard L. "Estimates of pain prevalence and severity in adults: United States, 2012." The Journal of Pain 16.8 (2015): 769-780.

Nakajima, H., et al. "Cervical angina: a seemingly still neglected symptom of cervical spine disorder?" Spinal cord 44.8 (2006): 509-513.

Neupane, M et al. Study of Anodic Oxide Films of Titanium Fabricated by Voltammetric Technique in Phosphate Buffer Media. Int. J. Electrochem. Sci., 4 (2009) 197-207.

Nielsen et al., "AC-Corrosion and Electrical Equivalent Diagrams", in: Proceedings of 5th International Congress, CeoCo, bruxelles, Belgium, 2000.

Schaldach, M, Fractal Coated Leads: Advanced Surface Technology of Genuine Sensing and Pacing, Progress in Biomedical Research, (2000): 259-272.

(56) References Cited

OTHER PUBLICATIONS

Scheiner, A., et al., "Imbalanced Biphasic Electrical Stimulation: Muscle Tissue Damage", Annals of Biomedical Engineering, 18 (1990): 407-425.
Specht, H. et al., Electrochemical properties and stability of PVD coatings for the application in cardiac and neurological stimulation, (2006).
Tjepkema Cloostermans, Marleen C., et al. "Effect of burst stimulation evaluated in patients familiar with spinal cord stimulation." Neuromodulation: Technology at the Neural Interface 19.5 (2016): 492-497.
Yang, Fei, et al. "Differential expression of voltage-gated sodium channels in afferent neurons renders selective neural block by ionic direct current." Science advances 4.4 (2018): eaaq1438 in 10 pages.

* cited by examiner

| Failure | Bias Current Monitor & Self Test | Cyclic VPP | Electrode Waveform Morphology Check | MCU/WD Voltage Supervision | Hardware Watchdog | Offline Impedance Check | MCU/WD Cross Check | Independent Charge Management Algorithms | Battery Seal* |
|---|---|---|---|---|---|---|---|---|---|
| Bias Error/IE Disconnect | ✓ | | | | | | | | |
| Electrode Disconnection | | | ✓ | | | | | | |
| Electrode Degradation | | ✓ | | | | | | | |
| VSTIM/VDD | | | | ✓ | | | | | |
| Current Source (ASIC) | ✓ | | ✓ | | | | | | |
| MCU HW | | | | | ✓ | | ✓ | ✓ | |
| MCU FW | | | | | ✓ | | ✓ | ✓ | |
| Coupling Cap Switch Failure | ✓ | | | | | | | | |
| ASIC Instrumentation Signal Chain | ✓ | | ✓ | | | | | ✓ | |
| Stim Cycle Shorting due to Power Loss | | | | | | | | | ✓ |

FIG. 7

PULSE GENERATION AND STIMULATION ENGINE SYSTEMS

INCORPORATION BY REFERENCE TO ANY PRIORITY APPLICATIONS

This application is a U.S. National Phase of International Application No. PCT/US2020/062077, filed Nov. 24, 2020, which claims the benefit of priority of U.S. Prov. Application No. 62/939,666, filed on Nov. 24, 2019, and U.S. Prov. Application No. 62/965,772, filed on Jan. 24, 2020, which are hereby incorporated by reference in their entireties. Any and all applications for which a foreign or domestic priority claim is identified in the Application Data Sheet as filed with the present application are hereby incorporated by reference under 37 CFR § 1.57.

BACKGROUND

This application relates, in some embodiments, to facilitating block, modulation or attenuation of biological signals through nerve tissue, including the processing of biological tissue in nervous system tissue, cardiac tissue, or other voltage-sensitive tissue.

The gate control theory of pain was developed in the 1960s and led to the advent of stimulation-based pain management therapies to reduce pain inputs from reaching the brain by selectively stimulating non-nociceptive fibers (non-pain transmitting fibers) in the spinal cord to inhibit transmission of pain stimuli to the brain (See Mendell, Constructing and Deconstructing the Gate Theory of Pain, Pain, 2014 February 155(2): 210-216). Current stimulation systems for spinal cord stimulation (SCS), which act on this gate control theory to indirectly reduce pain, typically have relied on stimulation signals in the <100 Hz frequency range, and recently in the kHz frequency range. Stimulation of the dorsal root ganglia, DRG, in a similar frequency range has also been employed to reduce segmental pain through the same mechanism.

However, technologies based on this premise have drawbacks as pain transmission inhibition is not complete and side effects such as paresthesia can be uncomfortable for patients. Therefore, it is desirable to have systems and methods of treating pain which more effectively block or attenuate pain signal transmission through pain fibers, or decrease the excitability of neurons which process pain signals, rather than indirectly reducing pain signals through gate-theory activation of non-nociceptive fibers, as well as avoid undesirable side effects. Furthermore, block or attenuation of neural tissue or neural activity has been implicated in not only affecting pain but also in the management of movement disorders, psychiatric disorders, cardiovascular health, as well as management of disease states such as diabetes.

SUMMARY

Various systems, devices, and methods are disclosed herein. In some variants, a neuromodulation device can perform in multiple electrical modulation modes with a single architecture. The neuromodulation device can include a power source. The neuromodulation device can include a control unit. The neuromodulation device can include a bipolar current generator that can be connected to at least one working electrode. The neuromodulation device can include stimulation circuitry that can include at least one blocking capacitor that can block direct current, at least one indifferent electrode switch that can be in electrical communication with at least one indifferent electrode, and/or at least one blocking capacitor switch in electrical communication to bypass at least one blocking capacitor. The device can include a first stimulation mode in which the current generator can deliver alternating current to the at least one working electrode and/or a second stimulation mode in which the current generator can deliver direct current to the at least one working electrode, both return electrodes absorbed through the indifferent electrode. In the first stimulation mode, the control unit can configure another current generator to route though a second working electrode and cause the at least one indifferent electrode switch to disable the electrical communication between the current generator and the at least one indifferent electrode, and at least one blocking capacitor is active to block direct current. In the second stimulation mode, the two current generators are configured such that an offset current from 0 µA to a 1,000 µA or more can pass through the indifferent electrode switch toward the indifferent electrode, and the control unit can cause the at least two blocking capacitor switches to disable the electrical communication between the current generator at the at least one blocking capacitor, thereby bypassing the at least two blocking capacitors.

In some variants, the direct current can include a ultra low frequency current.

In some variants, the ultra low frequency currents can be less than about 5 Hz.

In some variants, the ultra low frequency currents can be less than about 2 Hz.

In some variants, the ultra low frequency currents can be less than about 1 Hz.

In some variants, the alternating current can be high frequency alternating current.

In some variants, the high frequency alternating current can be at least about 1 kHz.

In some variants, the alternating current can be between about 5 Hz and about 1 kHz.

In some variants, the power source can include a battery.

In some variants, the control unit can include a first control unit and a second control unit that can run independent algorithms.

In some variants, the device can measure the offset current when the device is in the second stimulation mode.

In some variants, the device can measure cyclic Vpp of the at least one working electrode.

In some variants, the device can include a virtual ground that can be operably connected to the indifferent electrode where the virtual ground can be set to any level to minimize power dissipation.

In some variants, the device can include one or more of the following mitigation mechanisms selected from the group consisting of: (a) control system configured to measure bias currents from an indifferent electrode, and halt or change operation if the bias currents deviate outside of preset parameters; (b) control system configured to measure electrode voltage between any of a pair of working electrodes; working and reference electrodes; and working and indifferent electrodes; (c) control system configured to resolve electrode monitoring with respect to waveform transitions; and (d) control system configured to receive data regarding entire or components of electrode voltage subject to a statistical analysis based on electrode characteristics.

In some variants, the device can comprise all of the mitigation mechanism—(a) control system configured to measure bias currents from an indifferent electrode, and halt or change operation if the bias currents deviate outside of preset parameters; (b) control system configured to measure electrode voltage between any of a pair of working electrodes; working and reference electrodes; and working and indifferent electrodes; (c) control system configured to resolve electrode monitoring with respect to waveform transitions; and (d) control system configured to receive data regarding entire or components of electrode voltage subject to a statistical analysis based on electrode characteristics.

In some variants, a method of delivering electrical neuromodulation to electrically excitable tissue of a patient utilizing a therapeutic neuromodulation device is disclosed. The method can include delivering alternating current to at least one working electrode in electrical communication with the electrically excitable tissue. Delivering alternating current can include blocking direct current utilizing at least one blocking capacitor of the therapeutic neuromodulation device; and preventing electrical communication between the therapeutic neuromodulation device and at least one indifferent electrode.

In some variants, the method can include discontinuing delivering alternating current; and/or delivering direct current to the at least one working electrode and an offset current to the at least one indifferent electrode, wherein when delivering direct current includes bypassing the at least one blocking capacitors of the therapeutic neuromodulation device.

In some variants, the method can include discontinuing delivering direct current to the at least one working electrode and/or resuming delivering alternating current to the at least one working electrode. Resuming delivering alternating current can include blocking direct current utilizing the at least one blocking capacitor of the therapeutic neuromodulation device. The method can include preventing electrical communication between the therapeutic neuromodulation device and at least one indifferent electrode.

In some variants, the direct current can include ultra low frequency current.

In some variants, the ultra low frequency currents can be less than about 5 Hz.

In some variants, the ultra low frequency currents can be less than about 2 Hz.

In some variants, the ultra low frequency currents can be less than about 1 Hz.

In some variants, the alternating current can be high frequency alternating current.

In some variants, the high frequency alternating current can be at least about 1 kHz.

In some variants, the alternating current can be between about 10 Hz and about 1 kHz.

In some variants, the method can include measuring the offset current using the neuromodulation device.

In some variants, the method can include measuring cyclic Vpp of the at least one working electrode.

In some variants, a method of delivering electrical neuromodulation to electrically excitable tissue of a patient utilizing a therapeutic neuromodulation device is disclosed herein. The method can include delivering direct current to at least one working electrode and an offset current to at least one indifferent electrode, wherein when delivering direct current can include bypassing at least one blocking capacitor of the therapeutic neuromodulation device.

In some variants, the method can include discontinuing delivering the direct current to the at least one working electrode and the offset current to the at least one indifferent electrode. The method can include delivering alternating current to the at least one working electrode in electrical communication with the electrically excitable tissue. Delivering alternating current can include blocking direct current utilizing at least one blocking capacitor of the therapeutic neuromodulation device; and preventing electrical communication between the therapeutic neuromodulation device and at least one indifferent electrode.

In some variants, the method can include discontinuing delivering the alternating current. The method can include resuming delivering direct current to the at least one working electrode and the offset current to the at least one indifferent electrode, wherein when resuming delivering direct current can include bypassing the at least one blocking capacitors of the therapeutic neuromodulation device.

In some variants, the direct current can include ultra low frequency current.

In some variants, the ultra low frequency currents can be less than about 5 Hz.

In some variants, the ultra low frequency currents can be less than about 2 Hz.

In some variants, the ultra low frequency currents can be less than about 1 Hz.

In some variants, the alternating current can be high frequency alternating current.

In some variants, the high frequency alternating current can be at least about 1 kHz.

In some variants, the alternating current can be between about 10 Hz and about 1 kHz.

In some variants, the method can include measuring the offset current using the neuromodulation device.

In some variants, the method can include measuring cyclic Vpp of the at least one working electrode.

In some variants, a neuromodulation device configured to perform in multiple electrical modulation modes with a single architecture is disclosed herein. The device can include a power source. The device can include a control unit. The device can include a current generator that can be connected to at least one working electrode. The device can include a stimulation circuitry that can include at least one blocking capacitor that can block direct current, at least one indifferent electrode switch that can be in electrical communication with at least one indifferent electrode, and at least one blocking capacitor switch in electrical communication to bypass with the at least one blocking capacitor;

In some variants, the device can include a first stimulation mode in which the current generator can deliver alternating current to the at least one working electrode.

In some variants, the device can include a second stimulation mode in which the current generator can deliver direct current to the at least one working electrode, both return electrodes absorbed through the indifferent electrode.

In some variants, in the first stimulation mode, the control unit configures another current generator to route though a second working electrode and causes the at least one indifferent electrode switch to disable the electrical communication between the current generator and the at least one indifferent electrode, and at least one blocking capacitor can be active to block direct current.

In some variants, in the second stimulation mode, the two current generators are configured such that an offset current from 0 uA to 100 µA or more is configured to pass through the indifferent electrode switch toward the indifferent electrode, and the control unit causes the at least two blocking capacitor switches to disable the electrical communication between the current generator at the at least one blocking capacitor, thereby bypassing the at least two blocking capacitors.

BRIEF DESCRIPTION OF THE DRAWINGS

FIG. 7 illustrates a table of example mechanism and mitigations.

DETAILED DESCRIPTION

Figure 1:
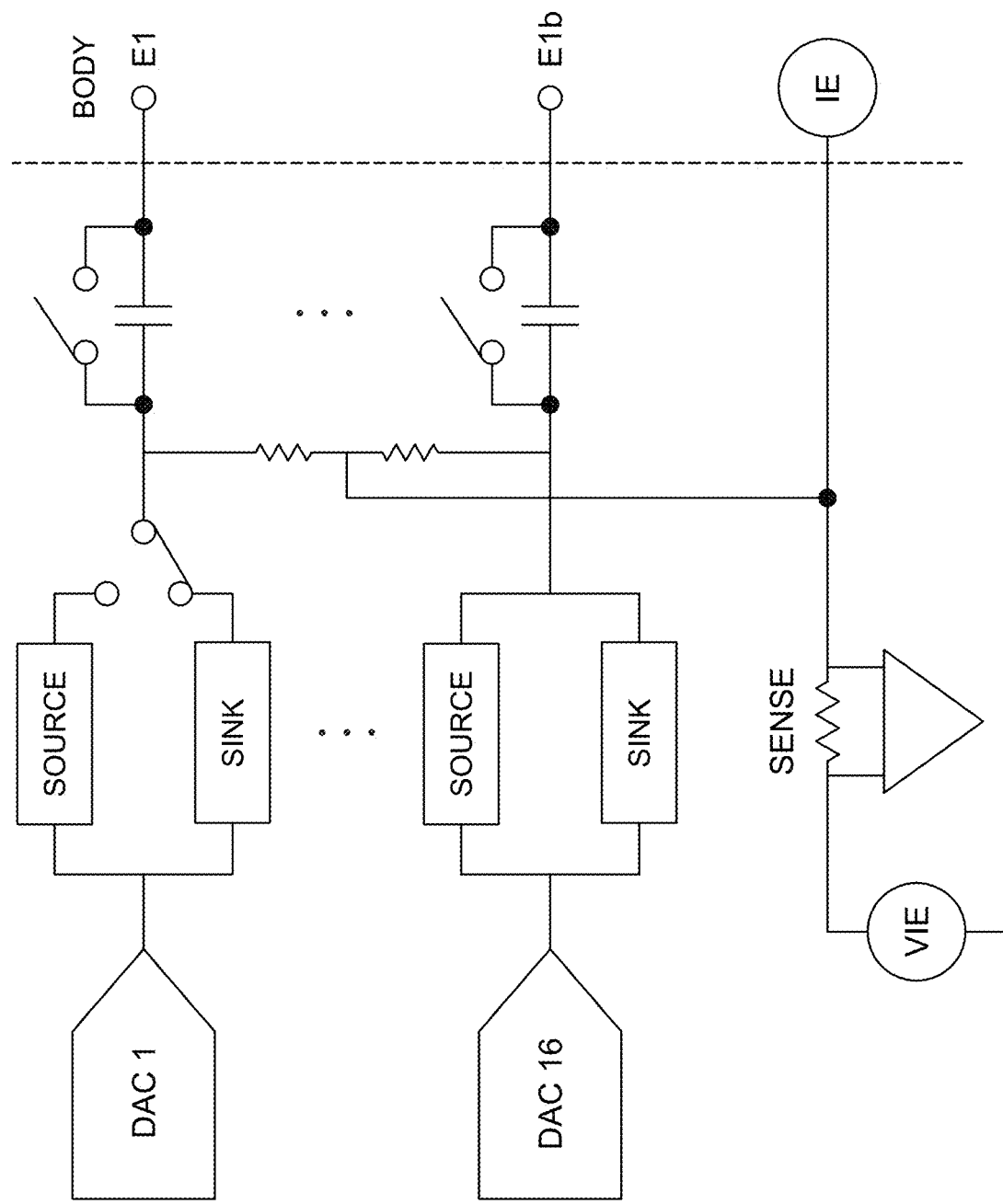
FIG. 1 illustrates a schematic of application-specific integrated circuit (ASIC).

This application relates, in some embodiments, to internal and external pulse generation and/or stimulation engine systems for facilitating block, modulation and/or attenuation of biological signals through nerve tissue, including the processing of biological tissue in nervous system tissue (including but not limited to neurons and glial cells), cardiac tissue, or other voltage-sensitive tissue. In some embodiments, either the anodic or cathodic phases of a delivered waveform to a patient, or both the anodic and cathodic phases can have a therapeutic effect on electrically excitable tissue, such as neural tissue for example.

In some embodiments, a pulse generation and/or stimulation engine system comprises any one or more of the features described in the disclosure.

In some embodiments, a pulse generation and/or stimulation engine method comprises any one or more of the features described in the disclosure.

Conventional stimulation systems can utilize capacitors to guarantee or promote fail-safe operation because they are reliable and low cost.

Some systems cannot use capacitors because they are fully integrated on silicon, the output frequencies are too low and capacitors would be too large, or some systems must pass direct current (DC). Some embodiments of systems can operate by providing a low frequency AC (LF-AC) waveform in conjunction with a low-level DC bias for the purpose of keeping the electrode operating range within a voltage window. The safety mechanisms in essence assure that both components stay within specification and that the resulting electrode voltages stay within the prescribed range as evaluated by, for example, at least two independent checking mechanisms. As for traditional and high frequency AC, capacitors can be switched in to protect against DC, and protection against switch failure can be afforded by assuring virtually no DC passes through the can, the only single-fault path that DC can take.

Disclosed herein, in some embodiments, are alternative embodiments to capacitors to increase patient safety and/or combined use of capacitors to provide protection, and in some cases for higher frequencies only.

Not to be limited by theory, the propagation of action potentials in electrically excitable tissue, e.g. neural tissue, leads to refractory periods on the order of milliseconds for sodium channels, typically between about 1 ms and about 20 ms, or between about 2 ms and about 5 ms for the combined absolute and relative refractory periods, thus very low frequency AC current waveforms with half periods meaningfully greater than this refractory period (e.g., greater than about 1 ms, 1.5 ms, 2 ms, 2.5 ms, 3 ms, 10 ms, 30 ms, 50 ms, 100 ms, 300 ms, 500 ms, 1000 ms, 2000 ms, 5000 ms, 6000 ms or more) and have sufficiently low differential rates (e.g. rise and fall-times) to not induce action potentials can also be used to create tissue blockade or attenuation, and will be perceived by electrically excitable tissue as a direct current stimulus. As such, direct current (DC) as defined herein is inclusive of low frequency AC current waveforms that are perceived as and functionally is direct current from the perspective of the tissue whose action potentials or neural processing are being modulated. The frequency could be, for example, less than about 10 Hz, 9 Hz, 8 Hz, 7 Hz, 6 Hz, 5 Hz, 4 Hz, 3 Hz, 2 Hz, 1 Hz, 0.5 Hz, 0.1 Hz, 0.05 Hz, 0.01 Hz, 0.005 Hz, 0.0001 Hz, or ranges including any two of the foregoing values so long as the direction of current flow is constant over at least the entire refractory period of the target tissue, or at least twice as long, or at least five times as long, or at least ten times as long as the refractory-causing membrane channel time constant (for example, fast sodium channel inactivation gate time constant).

In some embodiments, systems and methods can incorporate a variety of waveform frequencies, including high frequencies, e.g., about 1.2-50 kHz or higher; conventional frequencies, e.g., between about 20-1.2 kHz; low frequencies, e.g., between about 1-20 Hz; and ultra-low frequencies, e.g., below about 1 Hz. As noted elsewhere herein, direct current as defined herein is inclusive of low frequency AC current waveforms that are perceived as and functionally is direct current from the perspective of the tissue whose action potentials are being modulated.

Chronic pain is a significant burden on individuals and society as a whole. Nearly 50 million adults are estimated to have significant chronic or severe pain in the US alone. (See Nahin, Estimates of Pain Prevalence and Severity in Adults: United States, 2012, The Journal of Pain, 2015 August 16(8): 769-780) Worldwide, chronic pain is estimated to affect more than 1.5 billion people. (Borsook, A Future Without Chronic Pain: Neuroscience and Clinical Research, Cerebrum, 2012 June) While surgical techniques are sometimes applied to remove a specific source of pain, frequently due to impingement of a nerve, in many cases the precise cause of pain is not clear and cannot be reliably addressed via a surgical procedure. Pain management can alternatively be addressed by overwhelming the central nervous system with stimulating signals that prevent registration of pain inputs (gate control theory of pain). Typically, this stimulation in the case of spinal cord stimulation (SCS) is performed using metal electrodes and alternating current (AC) stimulation to produce these additional stimulating signals to prevent pain sensation. However, one major drawback is the presence of paresthesia, a sensation of tingling in the innervated region downstream from the stimulated nerve. Methods to eliminate paresthesia which patients can find discomforting have led to different means of stimulation from conventional tonic SCS (~30-120 Hz) stimulation including high frequency stimulation (~10 kHz) and burst stimulation (e.g., five pulses at 500 Hz delivered 40 times per second). (Tjepkema-Cloostermans et al, Effect of Burst Evaluated in Patients Familiar With Spinal Cord Stimulation, Neuromodulation, 2016 July 19(5):492-497).

An alternative means to manage pain signaling to the central nervous system is to prevent conduction of the pain signals from the peripheral signal source by directly blocking or attenuating the pain signals as compared to masking the pain signals by generating alternative neural inputs to crowd out and inhibit pain signal transmission as in traditional SCS and gate theory. One means to do this is by applying a direct current (DC) to a nerve to prevent action potential (AP) generation and transmission. Because this does not stimulate the nerve as in traditional stimulation, paresthesia can be avoided. The mechanism leading to AP block has been attributed to a depolarization block or hyperpolarization block that deactivates the sodium channels required for an action potential event under the electrode site. (See Bhadra and Kilgore, Direct Current Electrical Conduction Block of Peripheral Nerve, IEEE Transactions on Neural Systems and Rehabilitation Engineering, 2004 September 12(3): 313-324). Wide dynamic range (WDR) neurons integrate pain signals and have also been implicated as a contributing source of pain in patients, and application of direct current (DC) is well positioned to reduce this activity and may impact associated inhibitory and excitatory neurons that drive WDR activity.

The unmitigated use of direct current has long been known to be dangerous to nerve tissue due to creation of toxic species at the electrode-nerve interface. As such, systems and methods that facilitate safe delivery of direct current therapy would be highly desirable. In some embodiments, systems and methods can be configured to treat nociceptive pain. In some embodiments, systems and methods of treating pain and other medical can involve selective blockade of antero-lateral column tissue in the spinal cord. Furthermore, some embodiments relate to systems and methods of treating pain by the aforementioned systems and methods, specifically through selective blockade of dorsal root tissue and/or dorsal root ganglia. Moreover, in some embodiments, disclosed herein are systems and methods of treating pain, specifically through blockade or attenuation of one or more peripheral nerves.

In some embodiments, systems and methods can safely block or attenuate pain signals (which includes modulation of pain processing) in the spinal column by delivering very low frequency stimulation in the epidural space for up to two weeks or more, to achieve clinically measurable pain reduction in patients with chronic low back pain who are candidates for spinal cord stimulation (SCS).

With targeted nerve block, pain from specific dermatomes and pain in regional body sites can be managed. A number of localized targets implicated in moderating pain signal transduction can be addressed. For example, both more centrally located nerve tissues such as the spinothalamic tract and dorsal root ganglion can be targeted to manage lower back pain, sciatica, and complex regional pain syndrome (CPRS) among other pain considerations.

In some embodiments, an electrode can include a contact comprising a high charge-capacity material. The electrode contact can have in some cases a geometric surface area of between about 1 mm$^2$ and about 10 mm$^2$, or about 1 mm$^2$, 2 mm$^2$, 3 mm$^2$, 4 mm$^2$, 5 mm$^2$, 6 mm$^2$, 7 mm$^2$, 8 mm$^2$, 9 mm$^2$, 10 mm$^2$, 20 mm$^2$, 50 mm$^2$, 100 mm$^2$, or ranges including any two of the foregoing values. The electrode contact itself can be fabricated of a high charge capacity material, such as those described, for example, in U.S. Pat. No. 10,071,241 to Bhadra et al., which is hereby incorporated by reference in its entirety. Alternatively, the electrode contact can comprise a base at least partially, or entirely coated with a high charge capacity material. In some embodiments, a high charge capacity material can have a Q value of at least about 25, 50, 100, 200, 300, 400, 500, 1,000, 2,500, 5,000, 10,000, 50,000, 100,000, 500,000, or more µC, or ranges including any two of the foregoing values. The Q value of an electrode contact can refer to the total amount of charge that can be delivered through an electrode contact before the electrode contact begins generating irreversible chemical reactions at a rate that cannot be cleared through the body's nominal transport mechanism. These chemical reactions include but are not limited to oxygen or hydrogen evolution, or dissolution of the electrode materials. Non-limiting examples of high charge capacity materials are platinum black, iridium oxide, titanium nitride, tantalum, silver chloride, poly(ethylenedioxythiophene) and suitable combinations thereof. The electrodes can comprise fractal coatings or high surface area formats in some embodiments. High charge capacity materials may be configured to be monolithic or as coatings on base substrates. Non-limiting examples of substrates for coating include stainless steel such as 304 and 316LVM, nickel-cobalt-chrome alloys such as MP35N®, platinum and platinum-iridium, titanium, nickel-titanium alloys such as Nitinol. In some embodiments, the electrodes can include tantalum coated with titanium nitride. Tantalum as one non-limiting example can be a particularly advantageous material for its superior radiopacity, thus allowing for improved implantation, verification, and/or removal of implantable neuromodulation devices. In some embodiments, the electrodes can include one or more of titanium nitride, tantalum, and MP35N. To generate more surface area for the electrochemical reactions to occur, the traditional electrodes may be made from high surface area to volume structures such as roughened surfaces, woven surfaces, patterned surfaces, reticulated foam structures, porous sintered bead structures, nano- or micro-patterned structures to expose additional material surface area. In some embodiments, the electrode can be a SINE (separated-interface nerve electrode) or EICCC (electron to ion current conversion cell) electrode in which an electrode is immersed in an electrolyte solution which is in contact with an ion-conductive material-electrolyte solution interface with an ion-conductive material that electrically contacts the cardiac tissue or area proximal to cardiac tissue, as described, for example, in U.S. Pat. No. 9,008,800 to Ackermann et al., and U.S. Pub. No. 2018/0280691 to Ackermann et al., which is hereby incorporated by reference in their entireties.

In some embodiments, disclosed herein are systems and methods for safely and efficaciously stimulating neural tissue that can advantageously utilize a variety of waveforms from DC to high frequencies. Stimulation with DC, although potentially very useful, has not been commercially utilized for neural modulation because neurostimulation systems capable of delivering DC safely for long periods of time have not been available. Available commercial systems prevent DC delivery to limit irreversible electrochemical reactions, relying on charge balancing mechanisms. These systems can include blocking the DC component with capacitors, blocking capacitors, or mechanisms that remove charge accumulation at the end of a stimulation cycle. While reliable, typical capacitors limit charge to less than about one millicoulomb (mC) per phase, disallowing the use of ultra-low frequency signals at large charge magnitudes in excess of this charge capacity. The other widely utilized technique relies on actively balanced current sources, but these require redundancy to be fault tolerant and typically do not deliberately control electrode voltages important for some electrode technologies and have not been shown to be advantageous for long-term high charge delivery. Active systems in conjunction with coatings have been utilized in such devices as retinal implants to increase charge densities to about ~2 mC/cm², but these densities are still insufficient to allow use of very high charge per phase waveforms required by DC or very low frequency waveforms with sufficient current amplitude.

Some embodiments involve high surface area electrode coatings in conjunction with a bias current such as, for example, a DC bias to maintain the electrode voltages in the optimal range for a particular electrode material for long term operational durability. This approach can boost the charge per phase from about 50 µC/cm² used in conventional systems to about or at least about 5,000 µC/cm², 25,000 µC/cm², 50,000 µC/cm², and beyond in some cases without, for example, causing damage to either the electrode or the electrically excitable tissue. Systems and methods configured to allow for an intentional net bias current, e.g., DC bias, such as via a control system, can, in some cases, advantageously maintain the health of the high charge capacity electrodes (by preventing or inhibiting corrosion, e.g., oxidation, or other damage to the electrodes) as well as minimizing or preventing undesired reactions and generation of species such as OH—, H+ or oxygen free radicals that can lead to tissue damage. In some embodiments, the charge per anodic and/or cathodic phase is, for example, about 3,000 µC, 3,500 µC, 4,000 µC, 4,500 µC, 5,000 µC, 5,500 µC, 6,000 µC or more or less, such as between about 4,000 µC and about 5,000 µC per phase, and ranges including any two of the foregoing values.

In some embodiments, systems and methods for the delivery of current via implanted electrodes do not include capacitors such as blocking capacitors. In some embodiments, systems and methods for the delivery of current via implanted electrodes do not include resistors.

In some embodiments, the bias current is the current resulting from the summation of the currents being simultaneously delivered to the electrode contacts or working electrodes in proximity to the target excitable or voltage-sensitive tissue. In some embodiments, the bias current is equal in magnitude and opposite in polarity to the summation of the currents being simultaneously delivered to the electrode contacts or working electrodes. In some embodiments, the currents being simultaneously delivered to the electrode contacts or working electrodes can be adjusted to modulate the bias current.

In some embodiments, conventional AC systems, which can include an AC exclusive system, utilizes a capacitor on each/every output, e.g., electrode, to prevent delivery of DC to tissue. Conventional AC systems typically do not include bypass switches that can circumvent the capacitors, which may be needed for direct current (including at ultra-low frequencies as noted above, for example) waveform delivery.

In some embodiments, disclosed herein is a neuromodulation device configured to perform in multiple electrical modulation modes with a single architecture. The device can include, for example, a power source; a control unit; and/or one or more current generators (e.g., monopolar and/or bipolar) configured to be connected to at least one, two, three, four, or more working electrodes.

In some embodiments, a device can include stimulation circuitry including at least one, two, or more blocking capacitors configured to block direct current, at least one, two, or more indifferent electrode switches configured to be in electrical communication with at least one, two, or more indifferent electrodes, and at least one, two, or more blocking capacitor switches in electrical communication to bypass the at least one, two, or more blocking capacitors.

The device can include a first stimulation mode in which the current generator is configured to deliver alternating current to the at least one working electrode, and a second stimulation mode in which the current generator is configured to deliver direct current to the at least one working electrode, both return electrodes absorbed through the indifferent electrode.

In some embodiments, in the first stimulation mode the control unit configures another current generator to route though a second working electrode and causes the at least one indifferent electrode switch to disable the electrical communication between the current generator and the at least one indifferent electrode, and at least one blocking capacitor is active to block direct current.

In some embodiments, in the second stimulation mode the two current generators are configured such that an offset current from, for example, 0 µA to a 1,000 µA or more is configured to pass through the indifferent electrode switch toward the indifferent electrode, and the control unit causes the at least two blocking capacitor switches to disable the electrical communication between the current generator at the at least one blocking capacitor, thereby bypassing the at least two blocking capacitors.

In some embodiments, a device can be configured such that alternating current of ultra low, conventional, or high frequencies can be delivered from a current generator to any number of working electrodes, while an anodic or cathodic bias current is delivered to any number of working electrodes, with the blocking capacitor switches configured to bypass the blocking capacitors, which can be advantageous for, for example, electrode longevity.

In some embodiments, application-specific integrated circuits (ASICs) including some embodiments herein are configured for low power, highly versatile AC stimulation. Some embodiments can add DC but may not necessarily be optimal for DC because the DAC (digital to analog converter) resolution is relatively low, limiting DC bias/offset selectivity (DC offsets can be, for example, as low as 1 µA while simultaneously providing stimulation currents as high as, for example, 25 mA on the same channel), and the power while running in DC mode is relatively high because the current may be on continuously (100% duty cycle) or substantially continuously whereas conventional AC stimulation pulses may be on 250 uS every 25 mS (1% duty cycle).

In some embodiments, in reference to FIG. 1, a DC and AC approach, using an application-specific integrated circuit (ASIC), can include a bypass switch around each output blocking capacitor such that current, e.g., DC can be delivered when the bypass switch is closed and charge balanced AC can be delivered when the bypass switch is open. This can be applied to each channel, such as, for example, channels 1 and 16. Accordingly, if the bypass switch fails and current flows due to imbalance in current sources to the tissue due to a short in the switch (or other cause), a "sense" safety mechanism ("sense" circuit shown in FIG. 1) can be used to detect excess current flowing through the system back through the indifferent electrode, e.g., IPG can, and then shut off the stimulation and/or take another safety action measure.

Figure 2:
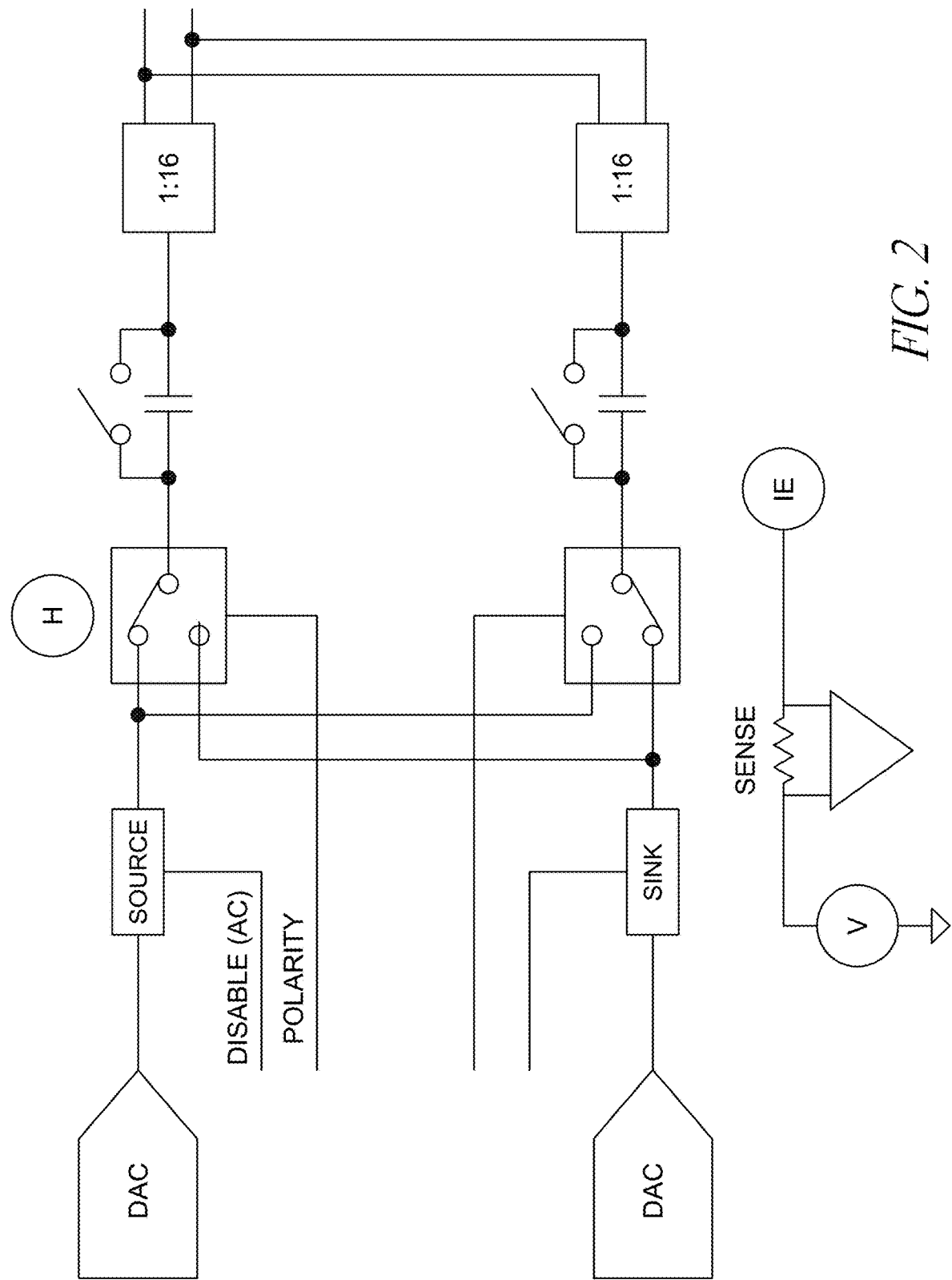
FIG. 2 illustrates a schematic of an ASIC with a DC and AC discrete approach.

In some embodiments, in reference to FIG. 2, a DC and AC discrete approach can be implemented with fewer components. For example, a blocking capacitor and bypass switches can be reduced to a single set between the source and the multiplexer (mux), which directs the current to a number of channels, such as for example 1 of 16 channels. In some embodiments, more than one set is used. In some embodiments, more or less than 16 channels can be used and/or the current can be directed to one or more channels. A second source and mux can also be used to sink or source the current for bipolar operation. This discrete approach can be advantageously simplified, which can reduce cost, manufacturing complexity, etc., by not including a capacitor and switch for each mux output (electrode). When the discrete approach described above and shown in FIGS. 3-4 is not implemented, a capacitor and switch for each channel may be needed (for example, 16 capacitor and switch pairs for a 16 channel system may be needed). A "sense" safety mechanism and IE can be used, as described in reference to FIG. 2, in the DC and AC discrete approach as well.

Figure 3:
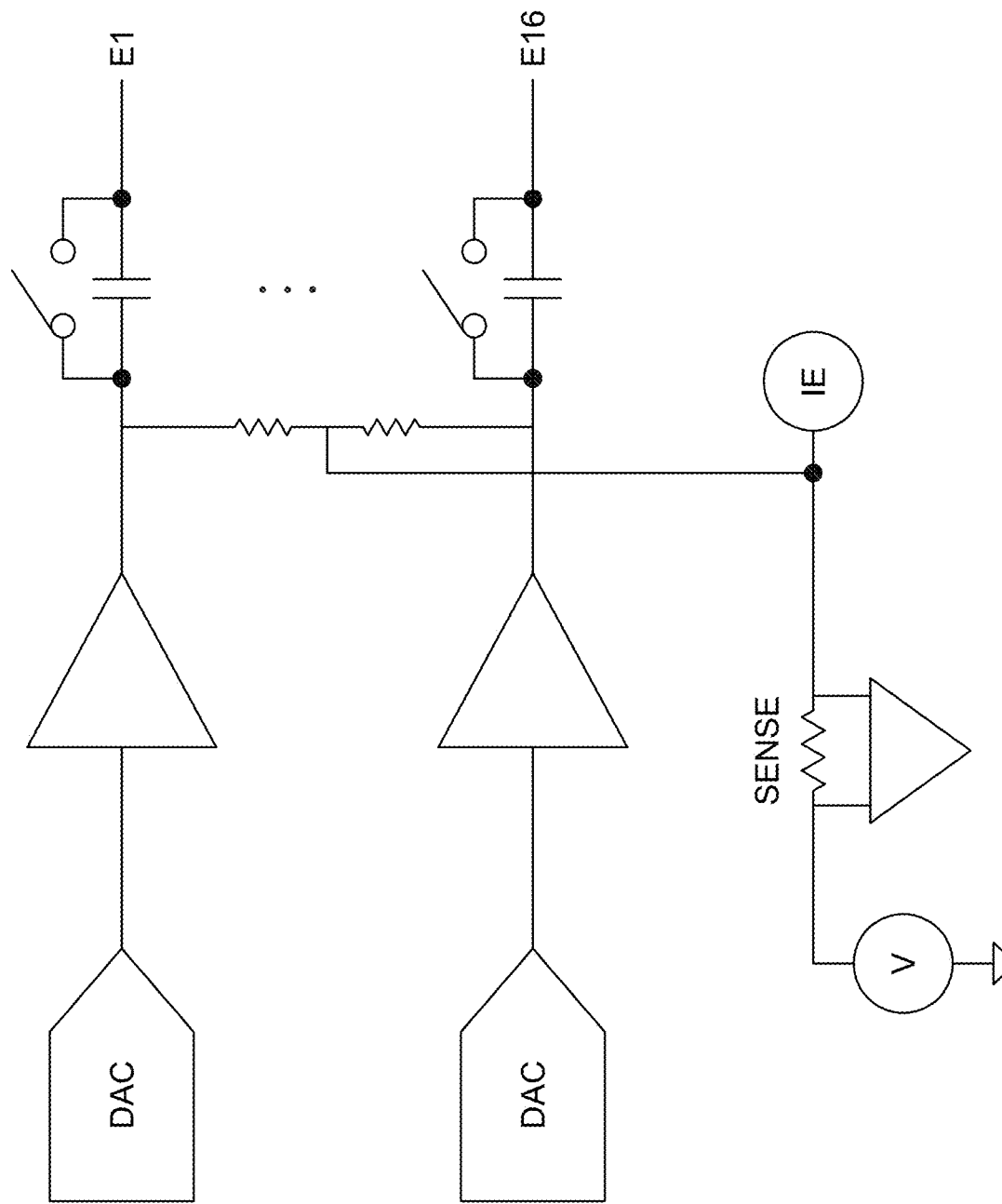
FIG. 3 illustrates a schematic of an ASIC adapted to deliver DC.

FIG. 3 schematically illustrates an embodiment of an ASIC adapted to deliver both DC and AC. DACs can directly control the current generators (sources and sinks) and external capacitor bypass switches have been included in the system to support DC. Because bypass switches, e.g., silicon bypass switches are exposed to the body, safety can be ensured, shutting down if any DC current is detected through the indifferent electrode (IE)/can.

Alternatively, both AC and DC systems can be implemented with a discrete system sharing common components. Some embodiments include a single bipolar channel that can be configured across any pair of electrodes in the system, such as 16 electrodes in some cases. The AC system can be configured to only include a single current sink and can be configured to be sufficiently fast to produce, in some embodiments, about 10 μS pulses requiring slew rates of about 10V/μS. This current source can be first routed through a cross point switch to alternate polarities across a set of capacitors that are then routed through a multichannel multiplexer, such as a 1 to 16 channel multiplexer for example. A single set of capacitors rather than a capacitor on each electrode can be used because safety again is confirmable by detecting DC current through the IE/CAN.

Figure 4:
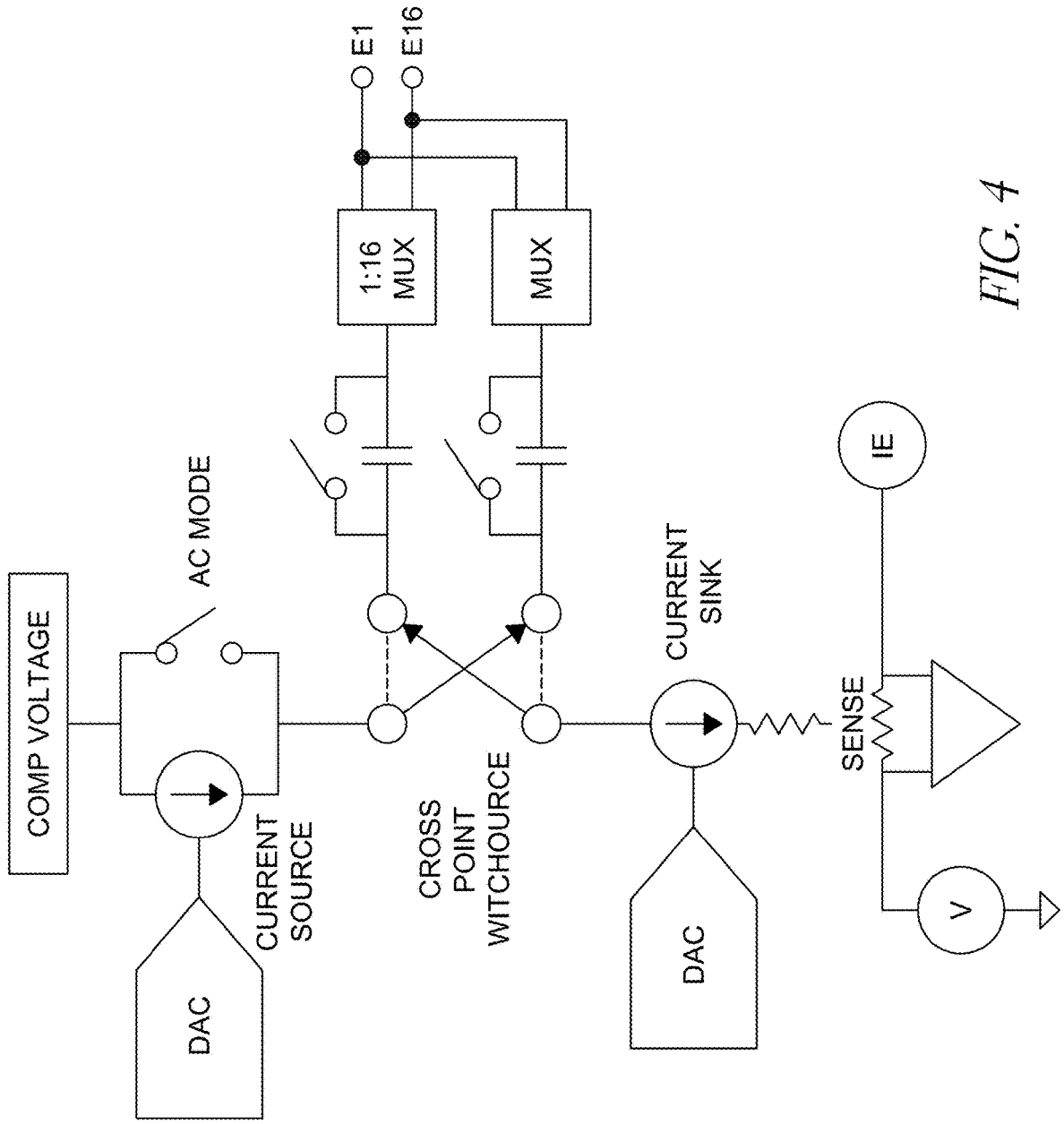
FIG. 4 illustrates a schematic of an ASIC adapted to deliver DC with a current source.

The AC Discrete Architecture embodiments as described above for example can be extended to handle DC with the addition of a current source, such as schematically illustrated in FIG. 4. To save power, this current source can be extremely slow requiring for example, about, or less than about 5, 4, 3, 2, or 1V/mS rather than a higher amount, such as, for example, 10V/μS or more required by the current sink. In addition, switches can be added to bypass the capacitors that may be absent with DC configurations. DC generally requires higher current resolution than AC to be able to accurately set the bias/offset current. As such, in some embodiments, the DAC resolution on both the current source and sink should be less than about 10, 9, 8, 7, 6, 5, 4, 3, 2, or 1 μA, or less than about 5 μA in some cases.

Figure 5:
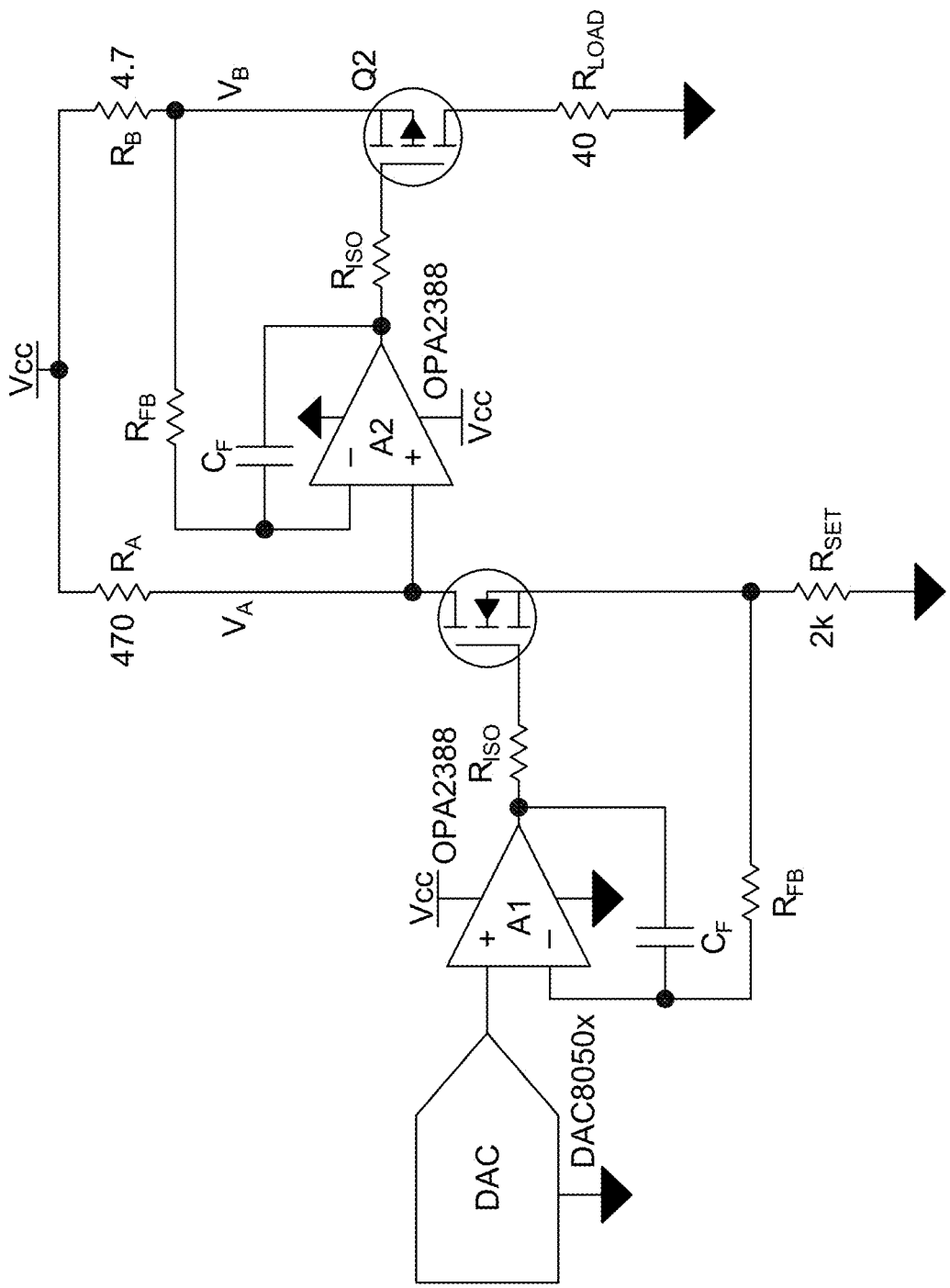
FIGS. 5 and 5B illustrates schematics of systems with a current source.

With respect to current sinks and current sources, in some cases, discrete current sinks can be simple and inexpensive to implement. A current source may in some cases be more involved and a circuit similar to that shown in FIG. 5A-5B) may be needed. Whereas the current sink implements AC and generally needs to be high performance, the current source generally only handles low speed DC and can operate much more slowly, advantageously reducing power significantly.

As described herein, some stimulation systems utilize capacitors to guarantee near fail-safe operation because they are passive, low cost, and generally reliable components. Some systems, however, cannot use (or it is at least less desirable to use) capacitors because they are fully integrated on silicon, the output frequencies can be too low, the system can be capable of passing DC, and/or capacitors can be too large.

Figure 5B:
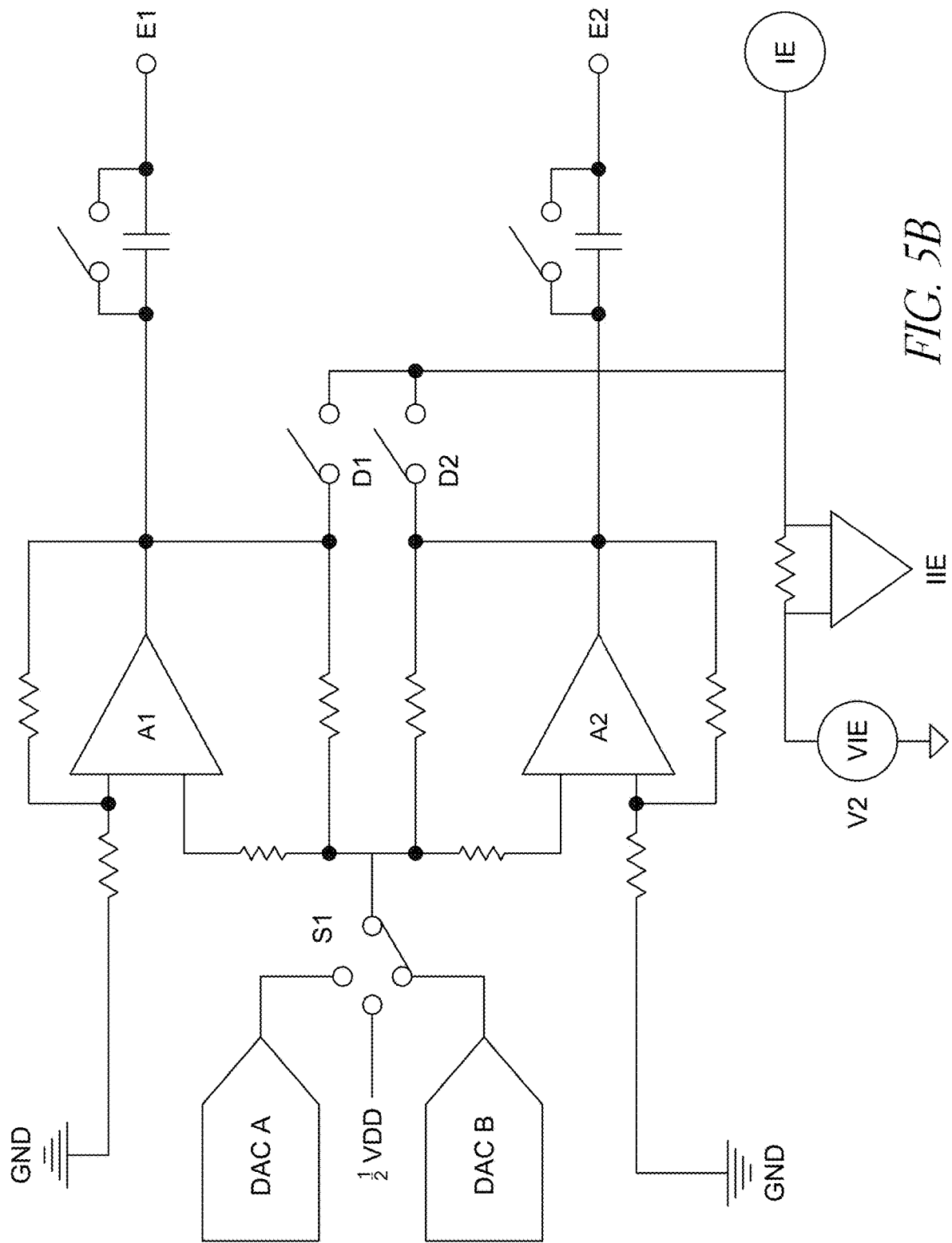

FIG. 5b is a schematic of a bipolar current generator that can be dynamically reconfigured to generate AC or DC stimulation. DAC A and B provide the stimulus amplitude. For slow moving DC stimulation DAC A and B are updated slowly (e.g., 100 Hz or less) with the bias added into each current. For AC DAC A and B are updated with the value of the activation and recovery current and S1 is switched to form fast AC activation and recovery pulses. Discharge switches are available to create other AC modes such as passive recharge.

Figure 6:
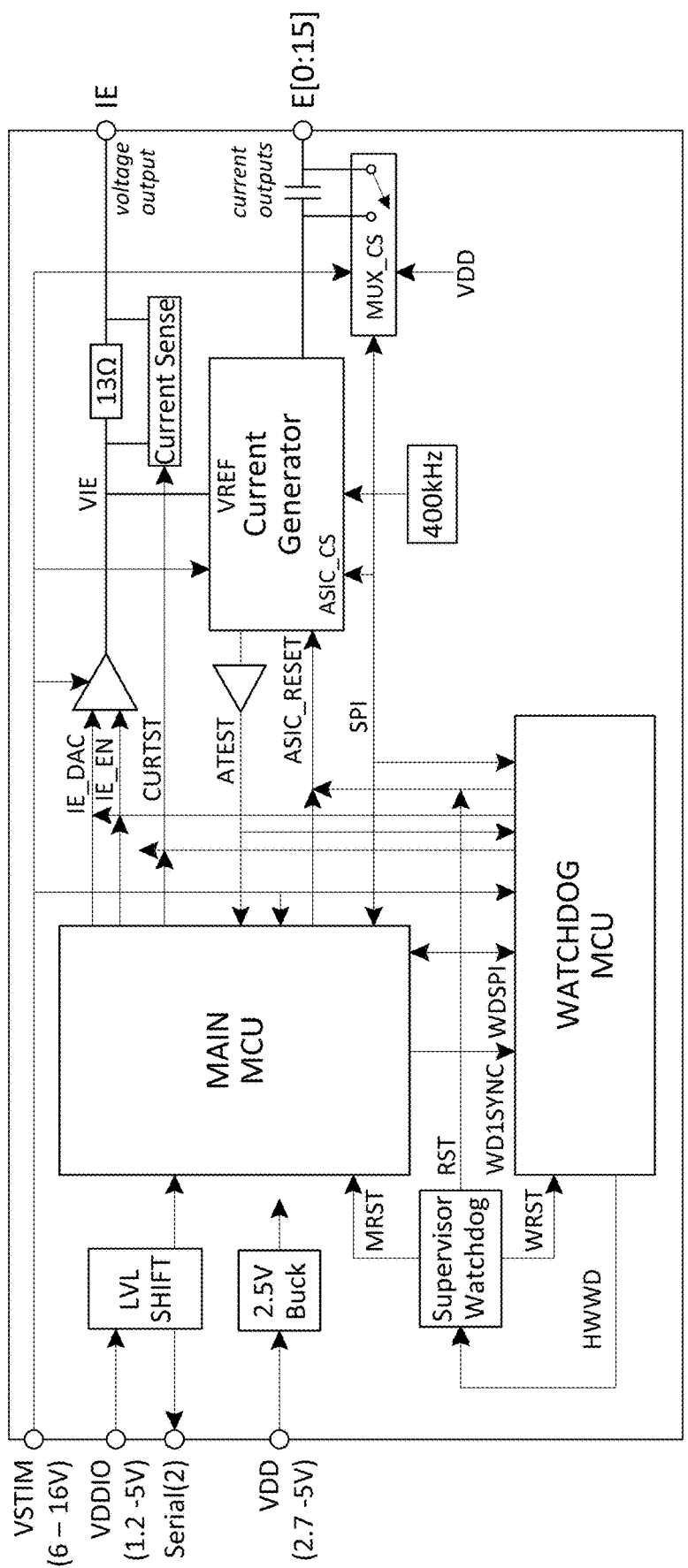
FIG. 6 illustrates a schematic of a fail-safe hybrid system.

FIG. 6 schematically illustrates a block diagram of a fail-safe hybrid system. The system can have a first control unit, e,g., main microcontroller unit (MCU) that is configured to implement a charge management algorithm through a current generator and an IE voltage output. The system can also include a second MCU, e.g., a watchdog MCU, also referred to herein as a monitoring MCU, that can have an independent charge management algorithm that can monitor the main MCU and can shut the system down in the event of a discrepancy. The main and watchdog MCUs can be configured to monitor the electrodes and system in a variety of ways which can include, for example, any number of: (1) monitoring electrode voltages to protect against electrode degradation and failures and electronic failures; (2) IE current monitoring to protect against device failures in AC or DC modes; and/or (3) voltage waveform morphology analysis to protect against device failures. During AC mode, blocking capacitors can be switched in-line. The main and watchdog MCU can cross-check each other for proper orientation. The system can include a third MCU, e.g., a supervisor watchdog MCU that can prevent devices from being reset. In external non-implanted variants, only a clinician may be allowed to change batteries to avoid stim cycling termination when the electrodes are loaded with charge.

FIG. 7 shows a table of non-limiting potential failure mechanisms listed in rows and mitigation mechanisms in columns. A check mark indicates which mitigations protect against which failures, according to some embodiments. When failures occur, stimulation is stopped either immediately (instant off) or at the end of a stimulation cycle when finishing in a charged balance state is beneficial. For example, bias current monitor out of range protects from a surface electrode (IE) disconnection, a current source error, a coupling capacitor error, or instrumentation signal chain error resulting in instant off stimulation. Cyclic VPP out of range (e.g., 10 or other numbers of cycles) is a primary mechanism protecting from long term electrode degradation resulting in the stimulation being ended at the completion of a stim cycle. Waveform morphology violation (e.g., 10 or other numbers of cycles) protects against electrode disconnection, current source failure or an instrumentation error resulting in the stimulation cycle being ended at the completion of a stim cycle. MCU/WD voltage supervision protects against stimulation or other power supply issues and terminates stimulation immediately and possible power off. Hardware watchdog protection protects against firmware/MCU failures resulting in general reset and ending the stim cycle immediately. Offline impedance check—precheck to exclude failed electrode and insufficient electrode capacity. MCU/WD cross check assures that both MCUs are operating properly resulting in general reset and ending the stim cycle immediately. Independent charge management algorithms (two different algorithms with independent code bases) protect against firmware bugs and unanticipated algorithm deficiencies resulting in general reset and ending the stim cycle immediately.

In some embodiments, a device can include a virtual ground configured to be operably connected to the indifferent electrode where the virtual ground can be set to any level to minimize power dissipation.

In some embodiments, current used from the output multiplexers are measured to detect any failures in the active silicon components that are tied directly to the body to prevent unintended DC currents due to part failures that occur especially due to ESD discharge damage.

In some embodiments, a device comprises any number of the following mitigation mechanisms: (a) indifferent electrode current monitoring halts operation if the bias currents deviate from a preset minimum and maximum range, the current used can be processed with a statistical process to remove noise; (b) Electrode Voltage monitoring either from each working electrode to the indifferent electrode, each working electrode to a reference electrode, or between a pair of working electrodes; (c) Electrode monitoring is resolved either instantaneously or statistically across a preset time from, for example, 1 µs to 1 hour or more or less, or synchronized to waveform transitions, statistics can include: mean, median, variance, minimum, and/or maximum; (d) Electrode monitoring can examine the electrode voltages in their entirety or break it into components using either a filter mechanism or by subtracting out components based upon what is known about the electrode, e.g., what is measured or the specifications of the electrode. As one example, the aforementioned above filtered voltage—stimulation current*measured access resistance can be below a specified value.

Figure 8:
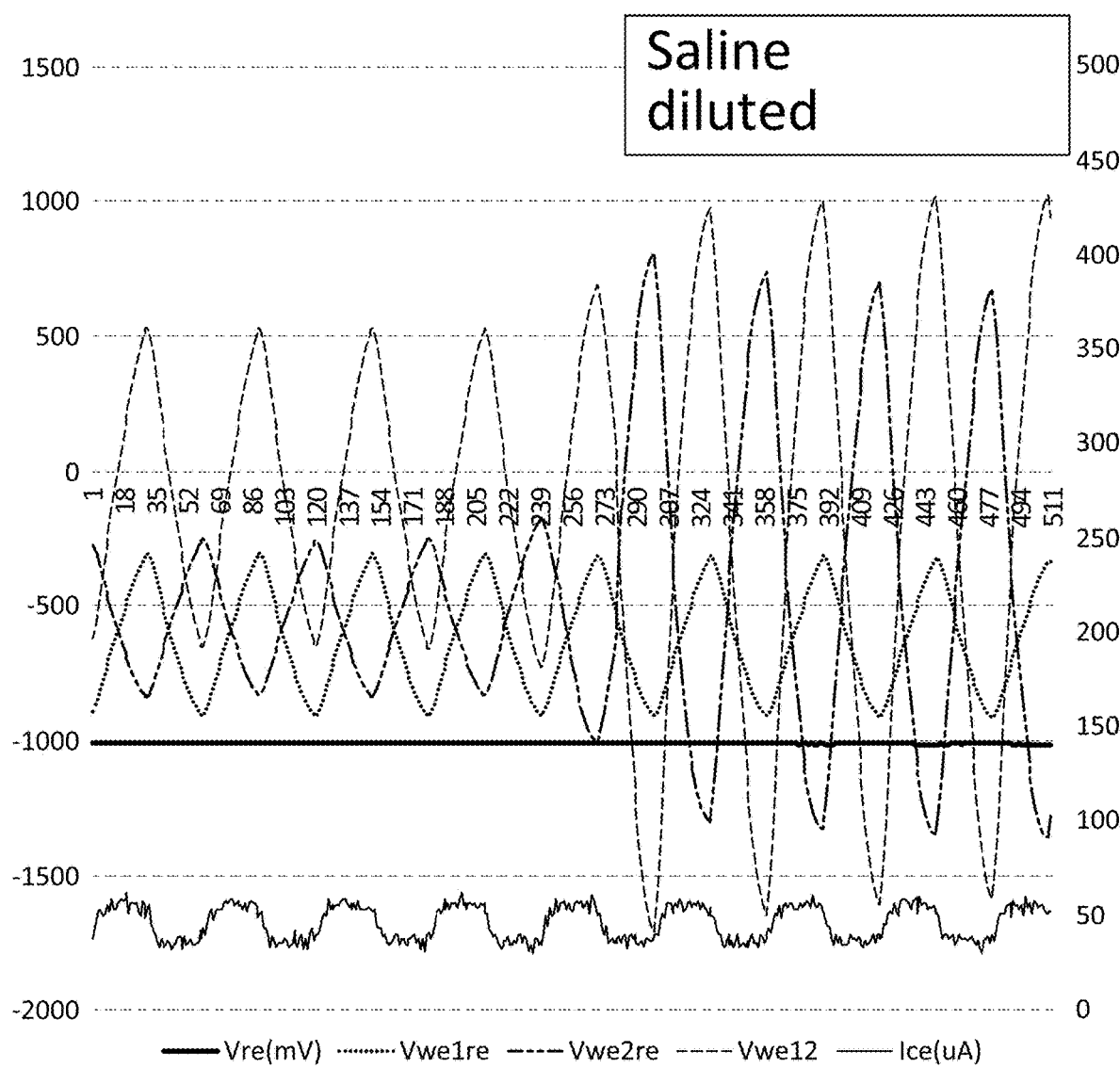
FIG. 8 illustrates a graph relating to lost capacity and voltage protections.

FIG. 8 illustrates a graph relating to lost capacity—which can be related to voltage protections. Cyclic VPP: VPP—2*RA*I, which can help ensure that peak voltage over a stimulation cycle stay within prescribed limits to assure an electrode has sufficient capacity over time. Electrode waveform morphology (sawtooth) can help ensure that the electrode voltage waveform is as expected for prescribed currents—which can help assure that the system is operating properly.

Figure 9A:
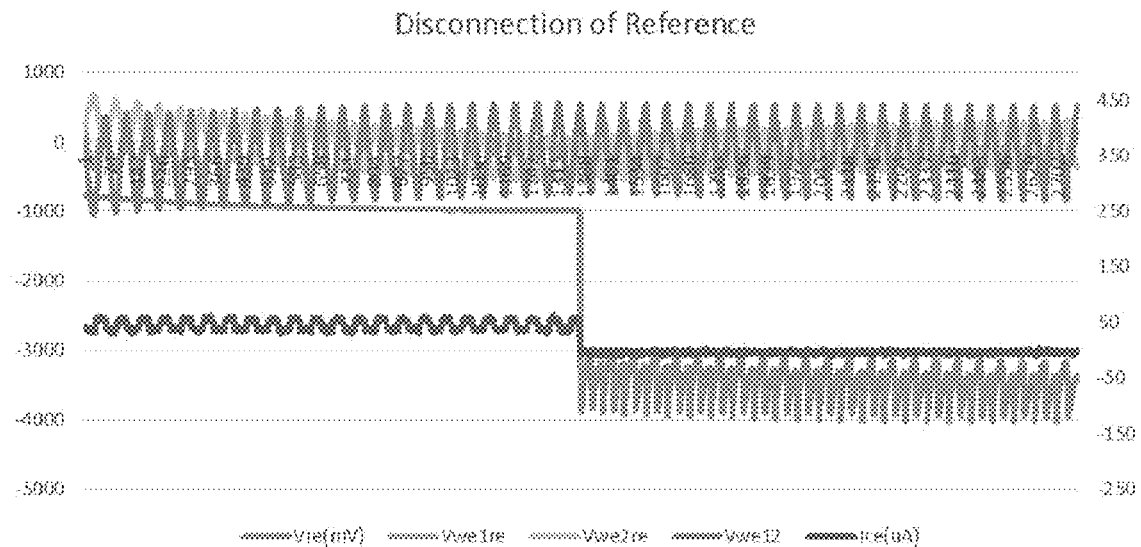
FIG. 9A illustrates a graph relating to the disconnection of a reference electrode.
Figure 9B:
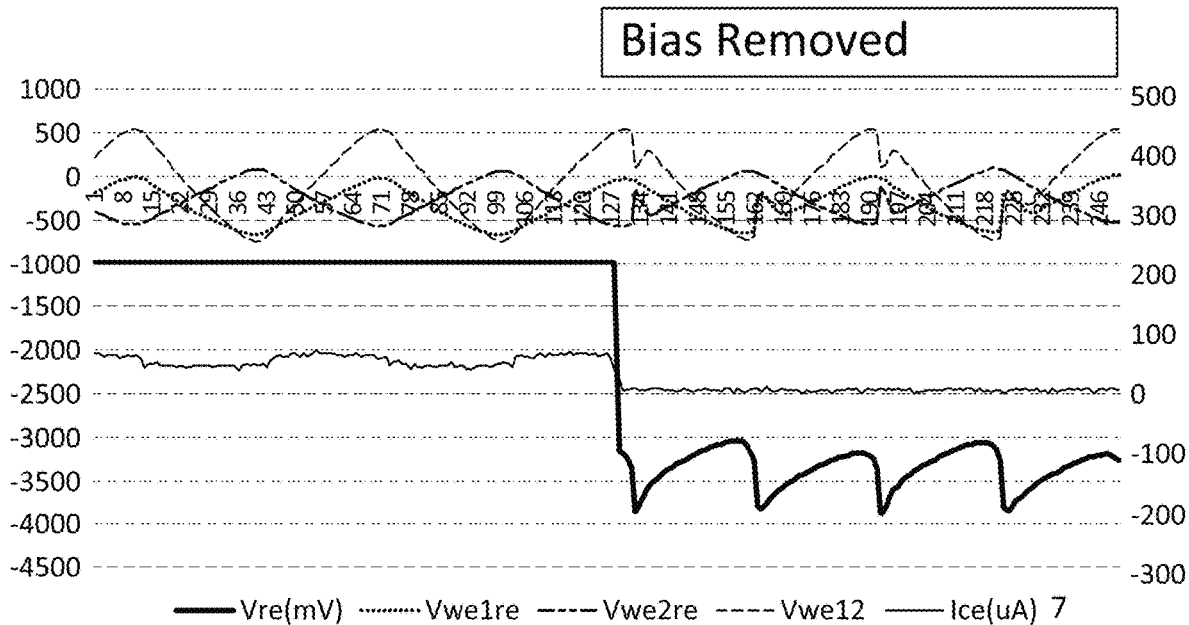
FIG. 9B illustrates a graph relating to bias removal.

FIGS. 9A and 9B relate to bias current monitoring. FIG. 9A illustrates a graph relating to the disconnection of a reference electrode. FIG. 9B illustrates a graph relating to the bias current being removed. Bias current monitoring can protect against various faults, which can include IE failure (open circuit or Hi-Z), WE failure (open circuit or Hi-Z), WE current source failure (Hi or Low), IE voltage source failure (no current of forces current source into failure), and/or capacitor bypass switch failure (current leakage or fail open). For DC specific modulation modes, the monitor can check that the bias is in the correct range (e.g., 25-75 µA). For AC specific modulation modes, the monitor can check that DC current is less than a predetermined value, such as, for example, ≤100 nA (e.g., electronic or multiple capacitor failures).

Figure 10:
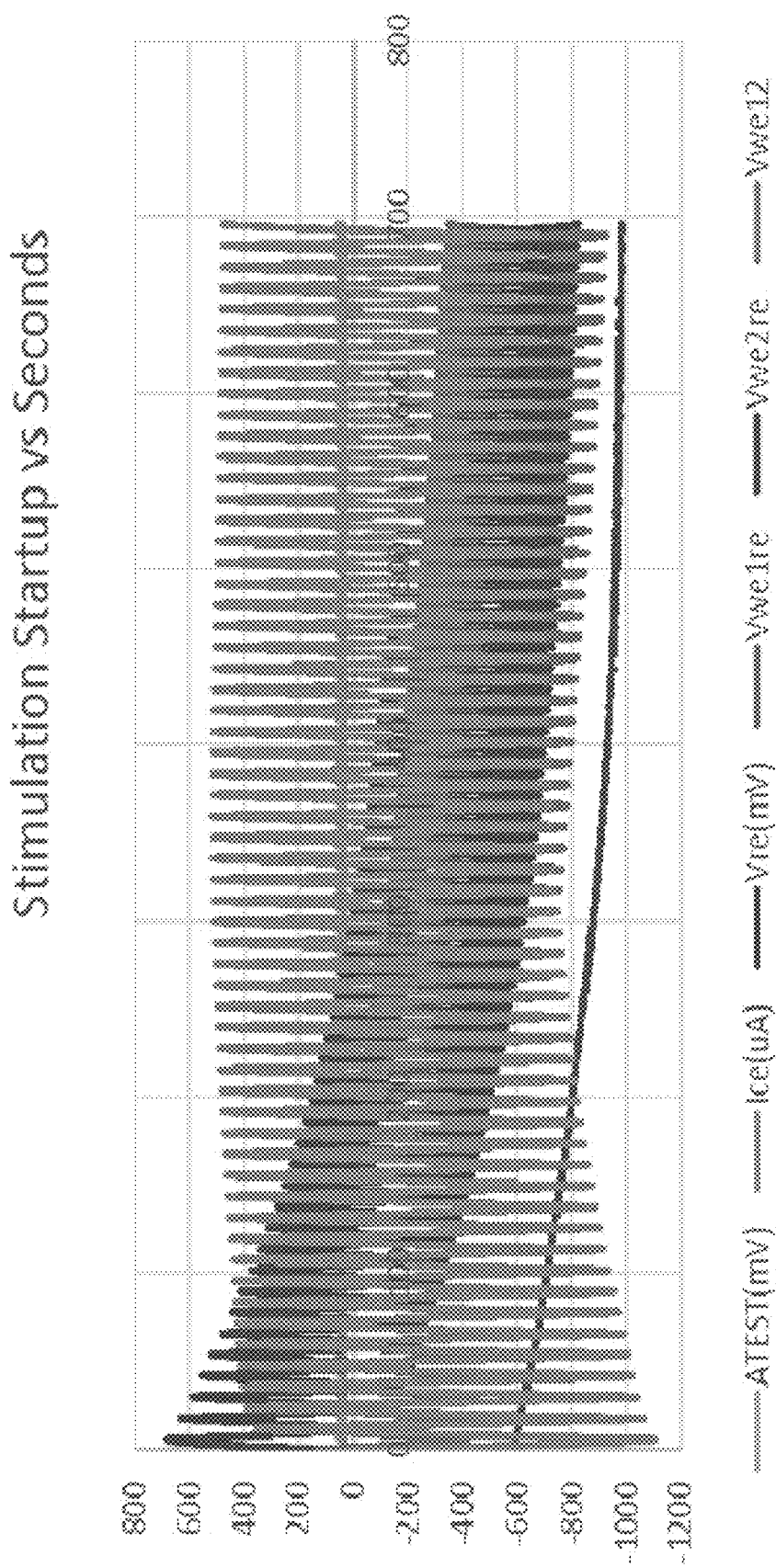
FIG. 10 illustrates a graph of stimulation startup against time in seconds.

FIG. 10 relates to reducing (e.g., minimizing) irrecoverable charge. FIG. 10 illustrates stimulation startup against time in seconds. The injection of bias current can place the electrode into an operational voltage range that can allow the charge and/or electrode life to be increased, such as maximized. The operating condition of the electrode can be determined, which can include determining that the electrode is in good operating condition. It can be determined that the electrode is in good operating condition by, for example: (1) determining (e.g., assuring) that the peak of the referenced voltage waveform is below a calculated or empirically calculated voltage and/or (2) integrating the voltage of a cycle as an indicator of irreversible charge and/or determine (e.g., assure) that it is under a specific threshold.

Figure 11:
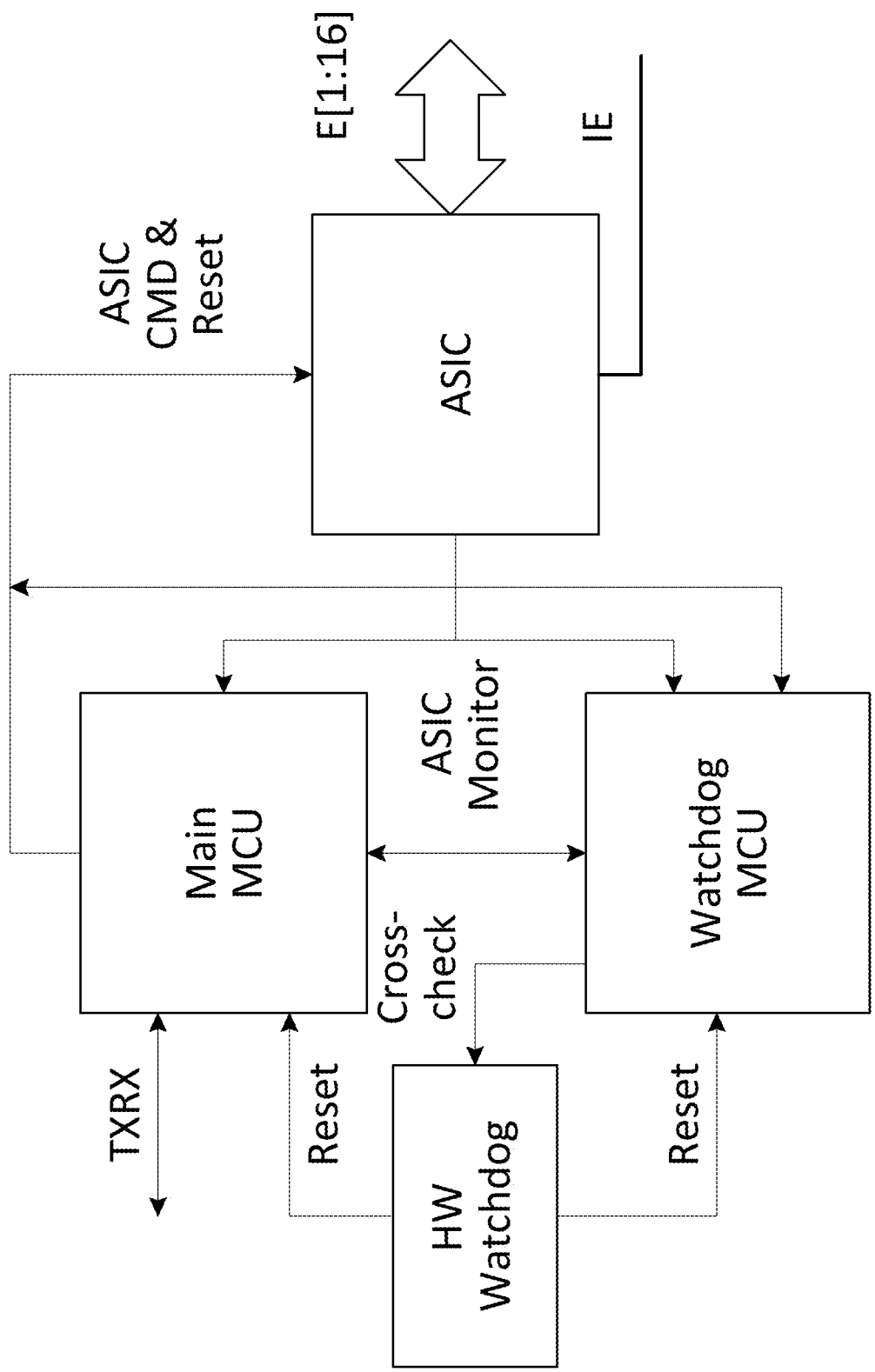
FIG. 11 illustrates a schematic relating to HW and FW fail-safe.

FIG. 11 illustrates an example block diagram relating to HW and FW fail-safe. Charge management algorithms—main MCU controls ASIC (or discrete current generator). MCU/WD voltage/current supervision—independent ADCs and algorithms in main and watchdog can be kept alive by Watchdog MCU assuring HW and FW are operational. MCU/WD cross check—Main and Watchdog MCU checkup on each other to assure HW and FW are operational. MCU/WD ASIC reset—either the main or watchdog MCU can reset ASIC when a problem is detected.

AC neurostimulation systems can rely primarily on isolating active circuitry from the body with series capacitors. In conjunction with internal discharge resistors/switches the capacitors not only protect from circuit failures but provide change balanced waveforms. High capacity electrode systems that utilize imbalanced charge biphasic waveforms that operate at ultra-low frequencies utilize DC stimulation and cannot readily utilize capacitors so alternate safety mechanisms must be implemented.

DC operates by providing an imbalanced charge ultra-low frequency imbalanced waveform that can operate the electrode within its protective voltage region where long term electrode capacity is optimized and preserved. The safety mechanisms can assure that resulting electrode voltages stay within the prescribed range as evaluated by at least two independent mechanisms, even in the case of one or more system fault, any detected faults can result in stimulation shutdown and power down of the stimulation engine.

To better understand the mitigations, the electrode can be modelled by a simplified Randles Cell; a series access resistance (Ra) and capacitance (Cdl) and polarization resistor (Rp or Rct). The polarization resistor because it is about >10× larger than Ra will be ignored in this treatment. The total voltage across the electrode (Vt) is equal to Ra*I+ Cyclic Vpp where Cyclic Vpp is the peak-to-peak voltage across the capacitive component (Cdl) of the electrode. Given this relationship, Va (from Ra×I) and Cyclic Vpp can be separated on each stimulation cycle using real-time measure of Vt and being able to calculate Ra.

To ensure tissue safety, operating electrodes within their electrode capacities can be important. Driving electrodes outside of their capacity eventually may reduce electrode capacity and facilitate reactions that may impact tissue health and cause irreversible electrochemical reactions. Cyclic Vpp is the primary measure of electrode health and is inversely proportional to the capacity of electrodes. Cyclic Vpp is expected to be fairly constant once the electrode has achieved steady state operation. If changes to the electrode over its life occur, these can be detected via Cyclic Vpp and stimulation can be adjusted to ensure operation within the electrode capacity, or the stimulation electrodes may be changed as needed.

The stimulation engine can include several mitigation mechanisms and can be categorized into firmware-based Charge Management Algorithm (CMA) Components that are firmware based and Hardware Mitigation Mechanisms—as summarized in the tables illustrated in FIG. 7.

Because firmware has a long-term probability of failure of 100%, the CMA Components can be implemented independently on independent multiple, e.g., main and safety MCUs. Two independent firmware images running two independent algorithms running on two independent processors can have a very low probability of failing within a finite time window. If failures are detected within 1 second and both systems have an independent average failure rate of once per day, the probability of failure in the 10-year life is $(1/86{,}400^2) \times 10y \times 365 d/y = 1/31{,}104{,}000$.

The foregoing description and examples has been set forth to illustrate the disclosure according to various embodiments and are not intended as being unduly limiting. The headings provided herein are for organizational purposes only and should not be used to limit embodiments. Each of the disclosed aspects and examples of the present disclosure may be considered individually or in combination with other aspects, examples, and variations of the disclosure. In addition, unless otherwise specified, none of the steps of the methods of the present disclosure are confined to any particular order of performance. References cited herein are incorporated by reference in their entirety.

While the methods and devices described herein may be susceptible to various modifications and alternative forms, specific examples thereof have been shown in the drawings and are herein described in detail. It should be understood, however, that the embodiments disclosed should cover modifications, equivalents, and alternatives falling within the spirit and scope of the various embodiments described herein and the appended claims.

Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some examples, acts or events can be performed concurrently, e.g., through multi-threaded processing, interrupt processing, or multiple processors or processor cores or on other parallel architectures, rather than sequentially.

The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed.

The various illustrative logical blocks, modules, processes, methods, and algorithms described in connection with the embodiments disclosed herein can be implemented as electronic hardware, computer software, or combinations of both. To clearly illustrate this interchangeability of hardware and software, various illustrative components, blocks, modules, operations, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The blocks, operations, or steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, an optical disc (e.g., CD-ROM or DVD), or any other form of volatile or non-volatile computer-readable storage medium known in the art. A storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that some examples include, while other examples do not include, certain features, elements, and/or states. Thus, such conditional language is not generally intended to imply that features, elements, blocks, and/or states are in any way required for one or more examples or that one or more examples necessarily include logic for deciding, with or without author input or prompting, whether these features, elements and/or states are included or are to be performed in any particular embodiment.

The methods disclosed herein may include certain actions taken by a practitioner; however, the methods can also include any third-party instruction of those actions, either expressly or by implication. For example, actions such as "positioning an electrode" include "instructing positioning of an electrode."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 hour" includes "1 hour." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure. The phrase "at least one of" is intended to require at least one item from the subsequent listing, not one type of each item from each item in the subsequent listing. For example, "at least one of A, B, and C" can include A, B, C, A and B, A and C, B and C, or A, B, and C.

What is claimed is:

1. A neuromodulation device configured to perform in multiple electrical modulation modes with a single architecture, comprising:
   a power source;
   a control unit;

a bipolar current generator configured to be connected to at least one working electrode;

stimulation circuitry comprising at least one blocking capacitor configured to block direct current, at least one indifferent electrode switch configured to be in electrical communication with at least one indifferent electrode, and at least one blocking capacitor switch in electrical communication to bypass at least one blocking capacitor;

wherein the device comprises a first stimulation mode in which the current generator is configured to deliver alternating current to the at least one working electrode, and a second stimulation mode in which the current generator is configured to deliver direct current to the at least one working electrode, both return electrodes absorbed through the indifferent electrode, wherein in the first stimulation mode the control unit configures another current generator to route though a second working electrode and causes the at least one indifferent electrode switch to disable the electrical communication between the current generator and the at least one indifferent electrode, and at least one blocking capacitor is active to block direct current, and wherein in the second stimulation mode the two current generators are configured such that an offset current is configured to pass through the indifferent electrode switch toward the indifferent electrode, and the control unit causes the at least two blocking capacitor switches to disable the electrical communication between the current generator at the at least one blocking capacitor, thereby bypassing the at least two blocking capacitors.

2. The neuromodulation device of claim 1, wherein the direct current comprises ultra low frequency current.

3. The neuromodulation device of claim 2, wherein the ultra low frequency currents are less than about 5 Hz.

4. The neuromodulation device of claim 2, wherein the ultra low frequency currents are less than about 2 Hz.

5. The neuromodulation device of claim 2, wherein the ultra low frequency currents are less than about 1 Hz.

6. The neuromodulation device of claim 1, wherein the alternating current is high frequency alternating current.

7. The neuromodulation device of claim 6, wherein the high frequency alternating current is at least about 1 kHz.

8. The neuromodulation device of claim 1, wherein the alternating current is between about 5 Hz and about 1 kHz.

9. The neuromodulation device of claim 1, wherein the power source comprises a battery.

10. The neuromodulation device of claim 1, wherein the control unit comprises a first control unit and a second control unit configured to run independent algorithms.

11. The neuromodulation device of claim 1, wherein the device is configured to measure the offset current when the device is in the second stimulation mode.

12. The neuromodulation device of claim 1, wherein the device is configured to measure cyclic Vpp of the at least one working electrode.

13. The neuromodulation device of claim 1, further comprising a virtual ground configured to be operably connected to the indifferent electrode where the virtual ground can be set to any level to minimize power dissipation.

14. The neuromodulation device of claim 1, wherein the device comprises one or more of the following mitigation mechanisms selected from the group consisting of:
(a). control system configured to measure bias currents from an indifferent electrode, and halt or change operation if the bias currents deviate outside of preset parameters;
(b). control system configured to measure electrode voltage between any of a pair of working electrodes; working and reference electrodes; and working and indifferent electrodes;
(c) control system configured to resolve electrode monitoring with respect to waveform transitions; and
(d) control system configured to receive data regarding entire or components of electrode voltage subject to a statistical analysis based on electrode characteristics.

15. The neuromodulation device of claim 14, comprising all of said mitigation mechanisms.

16. A method of delivering electrical neuromodulation to electrically excitable tissue of a patient utilizing a therapeutic neuromodulation device, comprising:
delivering alternating current to at least one working electrode in electrical communication with the electrically excitable tissue, wherein delivering alternating current comprises blocking direct current utilizing at least one blocking capacitor of the therapeutic neuromodulation device; and preventing electrical communication between the therapeutic neuromodulation device and at least one indifferent electrode;
discontinuing delivering alternating current;
delivering direct current to the at least one working electrode and an offset current to the at least one indifferent electrode, wherein when delivering direct current comprises bypassing the at least one blocking capacitors of the therapeutic neuromodulation device; and
discontinuing delivering direct current to the at least one working electrode, and resuming delivering alternating current to the at least one working electrode, wherein resuming delivering alternating current comprises blocking direct current utilizing the at least one blocking capacitor of the therapeutic neuromodulation device; and preventing electrical communication between the therapeutic neuromodulation device and at least one indifferent electrode.

17. A method of delivering electrical neuromodulation to electrically excitable tissue of a patient utilizing a therapeutic neuromodulation device, comprising:
delivering direct current to at least one working electrode and an offset current to at least one indifferent electrode, wherein when delivering direct current comprises bypassing at least one blocking capacitor of the therapeutic neuromodulation device;
discontinuing delivering the direct current to the at least one working electrode and the offset current to the at least one indifferent electrode; and
delivering alternating current to the at least one working electrode in electrical communication with the electrically excitable tissue;
wherein delivering alternating current comprises blocking direct current utilizing at least one blocking capacitor of the therapeutic neuromodulation device; and preventing electrical communication between the therapeutic neuromodulation device and at least one indifferent electrode.

18. The method of claim 17, further comprising:
discontinuing delivering the alternating current; and
resuming delivering direct current to the at least one working electrode and the offset current to the at least one indifferent electrode,
wherein when resuming delivering direct current comprises bypassing the at least one blocking capacitors of the therapeutic neuromodulation device.

19. The method of claim 17, wherein the alternating current is high frequency alternating current.

20. The method of claim 19, wherein the high frequency alternating current is at least about 1 kHz.

21. The method of claim 17, wherein the alternating current is between about 10 Hz and about 1 kHz.

* * * * *